(12) United States Patent
Calhoun et al.

(10) Patent No.: US 11,654,047 B2
(45) Date of Patent: May 23, 2023

(54) SYSTEMS AND METHODS FOR TREATING EYE DISEASES

(71) Applicant: J.D. Franco & Co., LLC, Plano, TX (US)

(72) Inventors: Michael Calhoun, Lighthouse Point, FL (US); Jeff Franco, Plano, TX (US); Robert M. Vidlund, Forest Lake, MN (US)

(73) Assignee: J.D. FRANCO & CO., LLC, Plano, TX (US)

( * ) Notice: Subject to any disclaimer, the term of this patent is extended or adjusted under 35 U.S.C. 154(b) by 381 days.

(21) Appl. No.: 16/932,401

(22) Filed: Jul. 17, 2020

(65) Prior Publication Data

US 2020/0345540 A1  Nov. 5, 2020

Related U.S. Application Data

(63) Continuation of application No. 16/789,658, filed on Feb. 13, 2020, now Pat. No. 10,751,215, which is a
(Continued)

(51) Int. Cl.
*A61F 9/007* (2006.01)
*A61M 25/10* (2013.01)
(Continued)

(52) U.S. Cl.
CPC ............... *A61F 9/007* (2013.01); *A61B 3/16* (2013.01); *A61B 5/026* (2013.01); *A61B 5/6866* (2013.01);
(Continued)

(58) Field of Classification Search
CPC ...... A61F 2/856; A61F 9/00781; A61F 9/007; A61F 2/966; A61F 2002/821
See application file for complete search history.

(56) References Cited

U.S. PATENT DOCUMENTS 2,690,595 A   10/1954 Raiche
3,367,101 A    2/1968 Garnet et al.
(Continued)

FOREIGN PATENT DOCUMENTS

EP   2 495 006        9/2012
WO   WO 98/52639 A1   11/1998
(Continued)

OTHER PUBLICATIONS

International Search Report and Written Opinion for International Application No. PCT/US2019/068758, dated May 29, 2020 (16 pages).
(Continued)

*Primary Examiner* — Julian W Woo
(74) *Attorney, Agent, or Firm* — Bookoff McAndrews, PLLC

(57) ABSTRACT

A method may include accessing a terminal branch of an ophthalmic artery through a face of a subject. Additionally, the method may include positioning a device within the ophthalmic artery of the subject and treating at least one of a blockage, a stenosis, a lesion, plaque or other physiology in at least one of the ophthalmic artery or a junction between an internal carotid artery and the ophthalmic artery.

19 Claims, 28 Drawing Sheets

Related U.S. Application Data continuation of application No. 16/583,508, filed on Sep. 26, 2019, now Pat. No. 10,682,253, which is a continuation of application No. 16/415,506, filed on May 17, 2019, now Pat. No. 10,470,925, which is a continuation of application No. 16/228,316, filed on Dec. 20, 2018, now Pat. No. 10,342,699, which is a continuation-in-part of application No. 15/971,809, filed on May 4, 2018, now Pat. No. 10,195,077, and a continuation-in-part of application No. PCT/US2017/051551, filed on Sep. 14, 2017, said application No. 15/971,809 is a continuation of application No. 15/681,075, filed on Aug. 18, 2017, now Pat. No. 9,987,164, said application No. 16/228,316 is a continuation-in-part of application No. 15/609,547, filed on May 31, 2017, now abandoned, said application No. 15/681,075 is a continuation of application No. PCT/US2017/051551, filed on Mar. 9, 2017, said application No. 15/609,547 is a continuation of application No. 14/385,496, filed as application No. PCT/US2013/053670 on Aug. 5, 2013, now abandoned.

(60) Provisional application No. 62/396,091, filed on Sep. 16, 2016, provisional application No. 62/395,294, filed on Sep. 15, 2016, provisional application No. 62/314,340, filed on Mar. 28, 2016, provisional application No. 62/305,991, filed on Mar. 9, 2016, provisional application No. 61/679,351, filed on Aug. 3, 2012.

(51) Int. Cl.

| | | |
|---|---|---|
| *A61F 2/966* | (2013.01) | |
| *A61B 17/12* | (2006.01) | |
| *A61F 2/856* | (2013.01) | |
| *A61M 27/00* | (2006.01) | |
| *A61B 17/3207* | (2006.01) | |
| *A61M 1/36* | (2006.01) | |
| *A61B 5/00* | (2006.01) | |
| *A61B 17/221* | (2006.01) | |
| *A61B 5/026* | (2006.01) | |
| *A61B 3/16* | (2006.01) | |
| *A61M 25/01* | (2006.01) | |
| *A61F 2/82* | (2013.01) | |
| *A61B 17/22* | (2006.01) | |
| *A61B 17/00* | (2006.01) | |
| *A61M 25/09* | (2006.01) | |
| *A61B 90/00* | (2016.01) | |
| *A61M 25/06* | (2006.01) | |
| *A61M 25/00* | (2006.01) | |

(52) U.S. Cl.
CPC .. *A61B 17/12109* (2013.01); *A61B 17/12136* (2013.01); *A61B 17/221* (2013.01); *A61B 17/320725* (2013.01); *A61B 17/320758* (2013.01); *A61F 2/856* (2013.01); *A61F 9/00781* (2013.01); *A61M 1/3621* (2013.01); *A61M 1/3627* (2013.01); *A61M 25/01* (2013.01); *A61M 25/1002* (2013.01); *A61M 25/104* (2013.01); *A61M 27/00* (2013.01); *A61B 17/12009* (2013.01); *A61B 2017/00986* (2013.01); *A61B 2017/22061* (2013.01); *A61B 2017/22079* (2013.01); *A61B 2090/064* (2016.02); *A61F 2/82* (2013.01); *A61F 2002/821* (2013.01); *A61M 25/0068* (2013.01); *A61M 2025/0186* (2013.01); *A61M 2025/0681* (2013.01); *A61M 2025/09008* (2013.01); *A61M 2025/1052* (2013.01); *A61M 2210/0612* (2013.01)

(56) References Cited

U.S. PATENT DOCUMENTS

| | | |
|---|---|---|
| 3,435,826 A | 4/1969 | Fogarty |
| 3,970,090 A | 7/1976 | Loiacono |
| 4,224,929 A | 9/1980 | Furihata |
| 4,403,612 A | 9/1983 | Fogarty |
| 4,445,897 A | 5/1984 | Ekbladh et al. |
| 4,794,931 A | 1/1989 | Yock |
| 4,857,045 A | 8/1989 | Rydell |
| 4,886,061 A | 12/1989 | Fischell et al. |
| 4,894,051 A | 1/1990 | Shiber |
| 4,898,575 A | 2/1990 | Fischell et al. |
| 4,926,858 A | 5/1990 | Gifford, III et al. |
| 4,936,835 A | 6/1990 | Haaga |
| 4,950,277 A | 8/1990 | Faar |
| 4,957,482 A | 9/1990 | Shiber |
| 4,979,939 A | 12/1990 | Shiber |
| 4,986,807 A | 1/1991 | Faar |
| 5,000,185 A | 3/1991 | Yock |
| 5,000,734 A | 3/1991 | Boussignac et al. |
| 5,007,896 A | 4/1991 | Shiber |
| 5,019,088 A | 5/1991 | Faar |
| 5,024,651 A | 6/1991 | Shiber |
| 5,026,384 A | 6/1991 | Farr et al. |
| 5,087,265 A | 2/1992 | Summers |
| 5,100,425 A | 3/1992 | Fischell et al. |
| 5,135,531 A | 8/1992 | Shiber |
| 5,176,693 A | 1/1993 | Pannek, Jr. |
| 5,292,332 A | 3/1994 | Lee |
| 5,313,949 A | 5/1994 | Yock |
| 5,314,438 A | 5/1994 | Shturman |
| 5,318,576 A | 6/1994 | Plassche et al. |
| 5,336,234 A | 8/1994 | Vigil et al. |
| 5,366,464 A | 11/1994 | Belknap |
| 5,395,311 A | 3/1995 | Andrews |
| 5,402,790 A | 4/1995 | Jang et al. |
| 5,409,454 A | 4/1995 | Fischell et al. |
| 5,415,634 A | 5/1995 | Glynn et al. |
| 5,419,761 A | 5/1995 | Narayanan et al. |
| 5,507,292 A | 4/1996 | Jang et al. |
| 5,554,119 A | 9/1996 | Harrison et al. |
| 5,709,701 A | 1/1998 | Parodi |
| 5,820,595 A | 10/1998 | Parodi |
| 5,897,567 A | 4/1999 | Ressemann et al. |
| 5,951,514 A | 9/1999 | Sahota |
| 5,972,019 A | 10/1999 | Engelson et al. |
| 6,010,522 A | 1/2000 | Barbut et al. |
| 6,146,370 A | 11/2000 | Barbut |
| 6,206,868 B1 | 3/2001 | Parodi |
| 6,302,908 B1 | 10/2001 | Parodi |
| 6,336,933 B1 | 1/2002 | Parodi |
| 6,344,054 B1 | 2/2002 | Parodi |
| 6,413,235 B1 | 7/2002 | Parodi |
| 6,423,032 B2 | 7/2002 | Parodi |
| 6,494,890 B1 | 12/2002 | Shturman et al. |
| 6,540,712 B1 | 4/2003 | Parodi et al. |
| 6,595,980 B1 | 7/2003 | Barbut |
| 6,623,471 B1 | 9/2003 | Barbut |
| 6,626,861 B1 | 9/2003 | Hart et al. |
| 6,641,573 B1 | 11/2003 | Parodi |
| 6,645,222 B1 | 11/2003 | Parodi et al. |
| 6,824,558 B2 | 11/2004 | Parodi |
| 6,827,726 B2 | 12/2004 | Parodi |
| 6,837,881 B1 | 1/2005 | Barbut |
| 6,855,162 B2 | 2/2005 | Parodi |
| 6,902,540 B2 | 6/2005 | Dorros et al. |
| 6,905,490 B2 | 6/2005 | Parodi |
| 6,908,474 B2 | 6/2005 | Hogendijk et al. |
| 6,929,634 B2 | 8/2005 | Dorros et al. |
| 6,936,053 B1 | 8/2005 | Weiss |
| 6,936,060 B2 | 8/2005 | Hogendijk et al. |
| 6,974,469 B2 | 12/2005 | Broome et al. |

(56) References Cited

U.S. PATENT DOCUMENTS

| | | |
|---|---|---|
| 7,195,611 B1 | 3/2007 | Simpson et al. |
| 7,214,201 B2 | 5/2007 | Burmeister et al. |
| 7,235,095 B2 | 6/2007 | Haverkost et al. |
| 7,309,334 B2 | 12/2007 | Von Hoffmann |
| 7,384,411 B1 | 6/2008 | Condado |
| 7,604,612 B2 | 10/2009 | Ressemann et al. |
| 7,806,906 B2 | 10/2010 | Don Michael |
| 7,867,273 B2 | 1/2011 | Pappas et al. |
| 7,901,445 B2 | 3/2011 | Wallace et al. |
| 7,927,347 B2 | 4/2011 | Hogendijk et al. |
| 8,123,779 B2 | 2/2012 | Demond et al. |
| 8,157,760 B2 | 4/2012 | Criado et al. |
| 8,267,956 B2 | 9/2012 | Salahieh et al. |
| 8,353,850 B2 | 1/2013 | Ressemann et al. |
| 8,409,237 B2 | 4/2013 | Galdonik et al. |
| 8,414,516 B2 | 4/2013 | Chang |
| 8,439,937 B2 | 5/2013 | Montague et al. |
| 8,545,432 B2 | 10/2013 | Renati et al. |
| 8,834,404 B2 | 9/2014 | Beaudin |
| 8,852,226 B2 | 10/2014 | Gilson et al. |
| 8,863,631 B1 | 10/2014 | Janardhan et al. |
| 9,078,682 B2 | 7/2015 | Lenker et al. |
| 9,241,699 B1 | 1/2016 | Kume et al. |
| 9,259,215 B2 | 2/2016 | Chou et al. |
| 9,265,512 B2 | 2/2016 | Garrison et al. |
| 9,987,164 B2 | 6/2018 | Calhoun |
| 10,195,077 B2 | 2/2019 | Calhoun et al. |
| 10,265,085 B2 | 4/2019 | Zaidat |
| 10,342,699 B2 | 7/2019 | Calhoun et al. |
| 10,682,253 B2 * | 6/2020 | Calhoun ............ A61M 25/1002 |
| 10,751,215 B2 * | 8/2020 | Calhoun ................ A61B 17/32 |
| 2001/0001114 A1 | 5/2001 | Tsugita et al. |
| 2002/0038103 A1 | 3/2002 | Estrada et al. |
| 2002/0077656 A1 | 6/2002 | Ginn et al. |
| 2002/0087128 A1 | 7/2002 | Paques et al. |
| 2002/0143291 A1 | 10/2002 | Slater |
| 2002/0151922 A1 | 10/2002 | Hogendijk et al. |
| 2002/0165573 A1 | 11/2002 | Barbut |
| 2003/0023200 A1 | 1/2003 | Barbut et al. |
| 2003/0023227 A1 | 1/2003 | Zadno-Azizi et al. |
| 2003/0199802 A1 | 10/2003 | Barbut |
| 2003/0199819 A1 | 10/2003 | Beck |
| 2003/0203958 A1 | 10/2003 | Kunz et al. |
| 2005/0149117 A1 | 7/2005 | Khosravi et al. |
| 2006/0089618 A1 | 4/2006 | McFerran et al. |
| 2006/0136022 A1 | 6/2006 | Wong, Jr. et al. |
| 2006/0259132 A1 | 11/2006 | Schaffer et al. |
| 2007/0026035 A1 | 2/2007 | Burke et al. |
| 2008/0027519 A1 | 1/2008 | Guerrero |
| 2008/0243229 A1 | 10/2008 | Wallace et al. |
| 2009/0018455 A1 | 1/2009 | Chang |
| 2009/0024072 A1 | 1/2009 | Criado et al. |
| 2009/0030323 A1 | 1/2009 | Fawzi et al. |
| 2009/0221961 A1 | 9/2009 | Tal et al. |
| 2010/0076365 A1 | 3/2010 | Riina et al. |
| 2010/0100045 A1 | 4/2010 | Pravongviengkham et al. |
| 2010/0125244 A1 | 5/2010 | McAndrew |
| 2010/0234884 A1 | 9/2010 | Lafontaine et al. |
| 2011/0143993 A1 | 6/2011 | Langer et al. |
| 2011/0152683 A1 | 6/2011 | Gerrans et al. |
| 2011/0152998 A1 | 6/2011 | Berez et al. |
| 2011/0160762 A1 | 6/2011 | Hogendijk et al. |
| 2011/0274748 A1 | 11/2011 | Robinson et al. |
| 2012/0046679 A1 | 2/2012 | Patel et al. |
| 2012/0078287 A1 | 3/2012 | Barbut |
| 2012/0101510 A1 | 4/2012 | Lenker et al. |
| 2013/0035628 A1 | 2/2013 | Garrison et al. |
| 2013/0197621 A1 | 8/2013 | Ryan et al. |
| 2013/0281788 A1 | 10/2013 | Garrison |
| 2014/0154246 A1 | 6/2014 | Robinson et al. |
| 2014/0222066 A1 | 8/2014 | Tegels |
| 2015/0025562 A1 | 1/2015 | Dinh et al. |
| 2015/0032121 A1 | 1/2015 | Janardhan et al. |
| 2015/0065804 A1 | 3/2015 | Kleyman |
| 2015/0231378 A1 | 8/2015 | Pepper |
| 2015/0272732 A1 | 10/2015 | Tilson et al. |
| 2015/0313607 A1 | 11/2015 | Zhadkevich |
| 2015/0359547 A1 | 12/2015 | Vale et al. |
| 2015/0359549 A1 | 12/2015 | Lenker et al. |
| 2015/0366580 A1 | 12/2015 | Lenihan et al. |
| 2016/0166754 A1 | 6/2016 | Kassab et al. |
| 2016/0317328 A1 | 11/2016 | Berez et al. |
| 2017/0164963 A1 | 6/2017 | Goyal |
| 2017/0239453 A1 | 8/2017 | Kawakita et al. |
| 2017/0326001 A1 | 11/2017 | Franco et al. |
| 2017/0348120 A1 | 12/2017 | Calhoun et al. |
| 2018/0132876 A1 | 5/2018 | Zaidat |

FOREIGN PATENT DOCUMENTS

| | | |
|---|---|---|
| WO | WO 98/53761 A1 | 12/1998 |
| WO | WO 00/54673 A1 | 9/2000 |
| WO | WO 03/018085 A2 | 3/2003 |
| WO | WO 2007/103464 A2 | 9/2007 |
| WO | WO 2012/162651 | 11/2012 |
| WO | WO 2014/022866 A1 | 2/2014 |
| WO | WO 2016/109586 A1 | 7/2016 |
| WO | WO 2016/149653 | 9/2016 |
| WO | WO 2017/156333 A1 | 9/2017 |
| WO | WO 2018/053121 A1 | 3/2018 |
| WO | WO 2018/106858 A1 | 6/2018 |

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

(56) References Cited

OTHER PUBLICATIONS

Yamane, T. et al., "The technique of ophthalmic arterial infusion therapy for patients with intraocular retinoblastoma," International Journal of Clinical Oncology, Apr. 2004; vol. 9, Issue 2, pp. 69-73.
Zeumer, H. et al., "Local intra-arterial fibrinolytic therapy in patients with stroke: urokinase versus recombinant tissue plagminogen activator (r-TPA)," Neuroradiology, 1993; 35: pp. 159-162.
Zipfel, P.F., et al., "The Role of Complement in AMD," Inflammation and Retinal Disease: Complement Biology and Pathology, Advances in Experimental Medicine and Biology, 2010, 703, pp. 9-24.
Examination Report No. 2 for AU Application No. 2013296195, dated Jun. 27, 2017 (6 pages).
Notice of Allowance for KR 20157005602, dated Sep. 25, 2017 (3 pages).
Loh, K. et al., "Prevention and management of vision loss relating to facial filler injections." Singapore Medical Journal, 2016; 57(8): 438-443.
International Search Report and Written Opinion for International Application No. PCT/US2017/0051551, dated Dec. 15, 2017 (14 pages).
International Search Report and Written Opinion for International Application No. PCT/US2017/0052901, dated Dec. 8, 2017 (9 pages).
Bird, B. et al., "Anatomy, Head and Neck, Ophthalmic Arteries," NCBI Bookshelf, a service of the National Library of Medicine, National Institutes of Health, Oct. 27, 2018, 5 pages. www.ncbi.nlm.nih.gov/books/NBK482317/.
Hattenbach, L. et al., "Experimental Endoscopic Endovascular Cannulation: A Novel Approach to Thrombolysis in Retinal Vessel Occlusion," Investigative Ophthalmology & Visual Science, Jan. 2012, vol. 53, No. 1, pp. 42-46.
Khan, T.T. et al., "An Anatomical Analysis of the Supratrochlear Artery: Considerations in Facial Filler Injections and Preventing Vision Loss," Aesthetic Surgery Journal, 2017, vol. 37(2), pp. 203-208.
Schumacher, M. et al., "Intra-arterial fibrinolytic therapy in central retinal artery occlusion," Neuroradiology (1993) 35: pp. 600-605.

Schwenn, O.K. et al., "Experimental Percutaneous Cannulation of the Supraorbital Arteries: Implication for Future Therapy," Investigative Ophthalmology & Visual Science, May 2005, vol. 46, No. 5, pp. 1557-1560.
Wang, R. et al., "Evaluation of Ophthalmic Artery Branch Retrograde Intervention in the Treatment of Central Retinal Artery Occlusion (CRAO)," Medical Science Monitor, 2017, 23: pp. 114-120.
Zhao, W. et al. "Three-Dimensional Computed Tomographic Study on the Periorbital Branches of the Ophthalmic Artery: Arterial Variations and Clinical Relevance," Aesthetic Surgery Journal, 2018, pp. 1-9.
International Search Report and Written Opinion for corresponding PCT/US2013/053670, dated Dec. 26, 2013 (16 pp.).
Hayreh et al. "Ocular Arterial Occlusive Disorders and Carotid Artery Disease," American Academy of Ophthalmology, 2017; vol. 1, No. 1: pp. 12-18.
Hayreh et al. "The Ophthalmic Artery," British Journal of Ophthalmology, 1962; 46, 65: pp. 65-98.
Hayreh, S.S., "The Ophthalmic Artery III. Branches," British Journal of Ophthalmology, 1962, 46, pp. 212-247.
International Search Report and Written Opinion for International Application No. PCT/US2018/031229, dated Jul. 27, 2018 (19 pages).
Mazur et al., Catheterization and Cardiovascular Diagnosis, vol. 31, Issue 1, Abstract (1994).
Aurboonyawat et al., "Indirect Carotid-Cavernous Sinus Fistulas Treated by Transvenous Approach Through the Superior Ophthalmic Vein: A Case Report and Technical Note," Siriraj Med. J., vol. 59, pp. 191-194, 2007.
Kleintjes, "Forehead anatomy: Arterial variations and venous link of the midline forehead flap," Journal of Plastic, Reconstructive & Aesthetic Surgery, vol. 60, Issue 6, pp. 593-606, 2007.
International Search Report and Written Opinion for International Application No. PCT/US2018/014766, dated Mar. 29, 2018 (7 pages).
Galassi et al. "Ocular Hemodynamics and Glaucoma Prognosis: A Color Doppler Imaging Study." Arch Ophthalmol; 2003; 121(12):1711-1715; doi:10.1001/archopht.121.12.1711.

\* cited by examiner

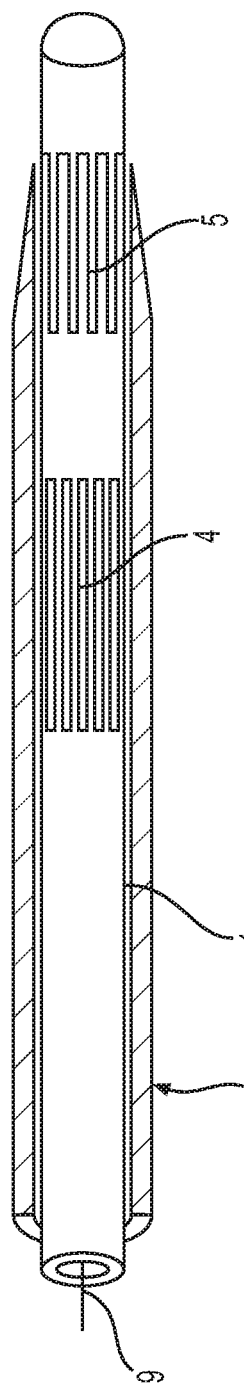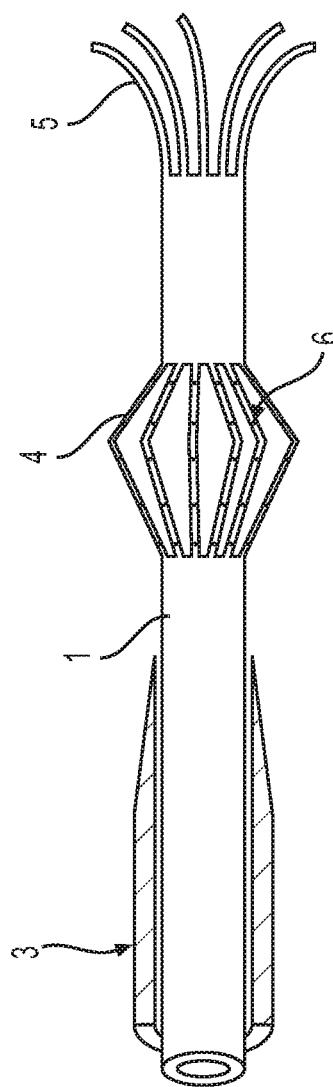
*FIG. 11A*
*FIG. 11B*

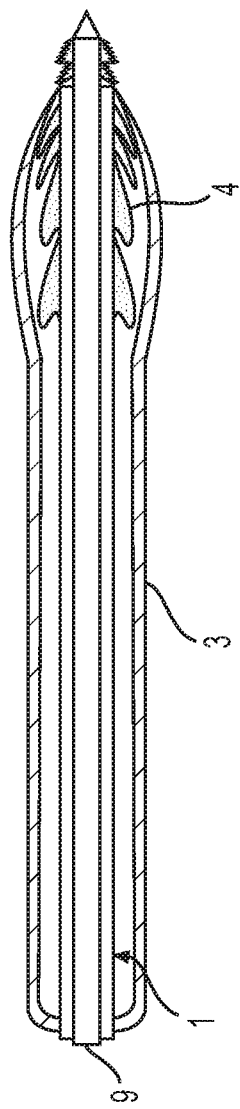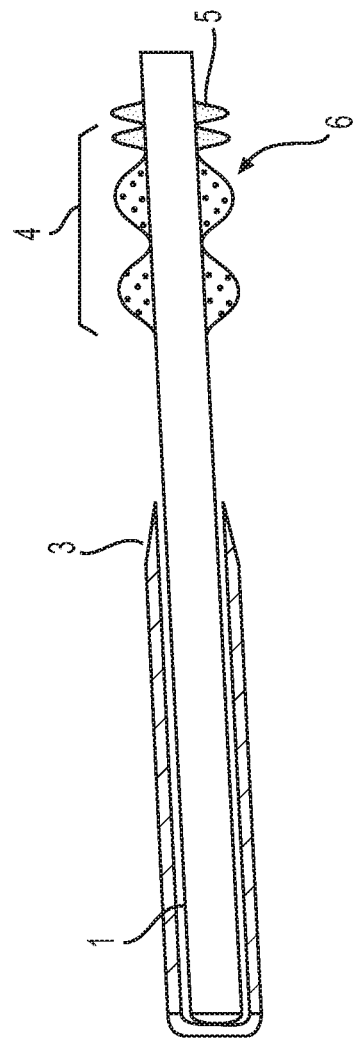
FIG. 15A
FIG. 15B

SYSTEMS AND METHODS FOR TREATING EYE DISEASES

CROSS-REFERENCE TO RELATED APPLICATIONS

This application is a continuation of U.S. patent application Ser. No. 16/789,658, filed on Feb. 13, 2020, now U.S. Pat. No. 10,751,215, which is a continuation of U.S. application Ser. No. 16/583,508, filed on Sep. 26, 2019, now U.S. Pat. No. 10,682,253, which is a continuation of U.S. application Ser. No. 16/415,506, filed May 17, 2019, now U.S. Pat. No. 10,470,925, which is continuation of U.S. application Ser. No. 16/228,316, filed Dec. 20, 2018, now U.S. Pat. No. 10,342,699, which is a continuation-in-part of U.S. application Ser. No. 15/971,809, filed on May 4, 2018, now U.S. Pat. No. 10,195,077, which is a continuation of U.S. application Ser. No. 15/681,075, filed on Aug. 18, 2017, now U.S. Pat. No. 9,987,164, which is a continuation application of International Application No. PCT/US2017/021673, filed on Mar. 9, 2017, which claims the benefit of priority of U.S. Provisional Application No. 62/396,091, filed on Sep. 16, 2016, U.S. Provisional Application No. 62/314,340, filed on Mar. 28, 2016, and U.S. Provisional Application No. 62/305,991, filed on Mar. 9, 2016, all of which are incorporated by reference herein in their entireties. U.S. application Ser. No. 16/228,316, filed on Dec. 20, 2018, to which this application claims priority, also claims priority to U.S. application Ser. No. 15/609,547, filed on May 31, 2017, which is a continuation of U.S. application Ser. No. 14/385,496, filed on Sep. 15, 2014, which is the U.S. National Stage Application of International Application No. PCT/US2013/053670, filed on Aug. 5, 2013, which claims the benefit of priority of U.S. Provisional Application No. 61/679,351, filed on Aug. 3, 2012, all of which are incorporated by reference herein in their entireties. U.S. application Ser. No. 16/228,316, filed on Dec. 20, 2018, to which this application claims priority, also claims priority to International Application No. PCT/US2017/051551, filed on Sep. 14, 2017, which claims the benefit of priority of U.S. Provisional Application No. 62/395,294, filed on Sep. 15, 2016, and U.S. Provisional Application No. 62/396,091, filed on Sep. 16, 2016, all of which are incorporated by reference herein in their entireties.

TECHNICAL FIELD

The present disclosure relates to treating an eye, including diseases and other conditions of the eye.

BACKGROUND

Diseases of the eye, specifically age-related macular degeneration (AMD), glaucoma, and diabetic retinopathy affect a large percentage of the population. However, current therapies are deficient in one or more aspects, necessitating improved approaches. The present disclosure addresses some or all of the problems found in current therapies.

BRIEF SUMMARY

The present disclosure is directed to treating an eye by using a device, method, system, or assembly as described herein. Specifically, the present disclosure is directed to treating eye diseases or conditions by using a device, method, system, or assembly as described herein.

For example, a method of the present disclosure may include accessing a terminal branch of an ophthalmic artery (OA) through a face of a subject, positioning a device within the OA of the subject, and treating at least one of a blockage, a stenosis, a lesion, plaque, or other physiology in at least one of the OA or a junction between an internal carotid artery (ICA) and the OA.

Examples of the method may include any one or more of the following features. The method may include inducing retrograde blood flow in the OA. The treating may include increasing a blood flow rate in the OA. The treating may include increasing a size of the at least one of the ICA or the OA. The increasing the size of the at least one of the OA or the junction between the ICA and the OA includes removing material. The increasing the size of the at least one of the OA or the junction between the ICA and the OA includes using a balloon in a balloon dilation procedure. The method may further include measuring a blood flow rate in the OA. The measuring the blood flow rate in the OA may include at least one of measuring a linear blood flow rate or a volumetric blood flow rate. The method may further include stopping antegrade blood flow in the OA. The accessing the terminal branch of the OA through the face of the subject may include accessing the OA through a facial skin of the subject. The accessing the terminal branch of the OA through the face of the subject includes accessing a supraorbital artery (SOA) or a supratrochlear artery (STA) of the subject.

In a further example, a method may include positioning a first device in a terminal branch of an OA through a face of a subject. Further, the method may include stopping antegrade flow in the OA and treating at least one of a blockage, a stenosis, a lesion, plaque, or other physiology in at least one of the OA or a junction between the ICA and the OA.

Examples of the method may include any one or more of the following features. The method may include inducing retrograde blood flow. The method positioning the first device in a terminal branch of the OA through the face of the subject may include positioning the first device in at least one of a SOA or a STA. The treating may include increasing a blood flow rate in the OA. The treating may include increasing a size of the at least one of the OA or the junction between the ICA and the OA. The increasing the size of the at least one of the OA or the junction between the ICA and the OA may include removing material. The increasing the size of the at least one of the OA or the junction between the ICA and the OA may include using a balloon. The method may include measuring a blood flow rate in the OA. The measuring the blood flow rate may include measuring at least one of a linear blood flow rate or a volumetric blood flow rate.

In a further example, a method may include locating a site in an arterial blood supply to an eye that compromises blood flow and contributes to an eye disorder. The method may further include accessing a terminal branch of an OA through a face of a subject and delivering a first device intravascularly to the site. Additionally, the method may include treating the site with the first device.

Examples of the method may include any one or more of the following features. The site may be in at least one of an OA or a junction between an ICA and the OA. The method may include at least one of stopping antegrade blood flow in the OA or inducing retrograde blood flow in the OA.

The present disclosure also includes intravascular medical devices and methods intended to sufficiently unblock or partially restore blood flow in a blocked or partially blocked artery such that nutrient(s) content is increased distal to the blockage. An embodiment of the disclosure is directed to devices and methods for restoring blood flow through the ostium. Another embodiment of the disclosure includes using these devices and methods to restore or increase blood flow to the eye or a portion thereof. Another embodiment includes restoring or increasing nutrient levels in the eye or a portion thereof. Restoring or increasing blood flow may include using these devices and methods, or equivalent devices and methods, but is not to be limited thereby.

The present disclosure also includes methods and devices for OA interventional procedures, such as stenting, angioplasty, and atherectomy, performed through a transcervical or transfemoral approach into the OA, either using an open surgical technique or using a percutaneous technique, such as a modified Seldinger technique. Some of these methods and devices are particularly useful in procedures which use reverse or retrograde blood flow.

For example, the disclosed methods and devices may include arterial access sheaths, closure devices, and interventional catheters. These methods and devices are useful for procedures utilizing any method of embolic protection, including distal filters, flow occlusion, retrograde flow, or combinations of these methods, or for procedures which do not use any method of embolic protection. Specific methods and devices for embolic protection are also described.

In other examples, the present disclosure describes methods and devices for enabling retrograde or reverse flow blood circulation in the OA in order to limit or prevent the release of emboli into the eye, and/or to employ various procedures for establishing, restoring, or increasing blood flow to the eye.

The present disclosure also describes a method for treating an OA, comprising forming a penetration in a wall of a carotid artery; positioning an arterial access sheath through the penetration; and causing retrograde blood flow from the OA into the sheath. In some embodiments, the method may also include inserting a delivery catheter through the sheath into a treatment site comprised of the ICA, the ostium, the junction between the ICA and the OA, the portion of the OA near the ICA, and/or the OA. In this aspect, causing retrograde flow may comprise connecting the arterial access sheath to a passive flow reversal circuit, or it may comprise connecting the arterial access sheath to an active aspiration source such as a syringe or suction pump.

In one example, the present disclosure includes a method of inducing retrograde blood flow which may include inserting a first arterial device into at least one of an ICA or a common carotid artery (CCA) of a subject. Additionally, the method may include inserting a second arterial device into a terminal branch of an OA of the subject. Further, the method may include inducing retrograde blood flow into the first arterial sheath and delivering at least some of the induced retrograde blood flow through the second arterial device and into the terminal branch of the OA.

Examples of the method may include any one or more of the following features. The inducing retrograde blood flow may include expanding an occlusion device of the first arterial device or compressing the at least one of the ICA or the CCA against a surface of the first arterial device. The method may further include inserting a vascular device within a vein of the subject. The vein may be an internal jugular vein (IJV) of the subject. The occlusion device may be a balloon. The induced retrograde blood flow may include retrograde blood flow within the OA of the subject. Inserting at least one of the first arterial device or the second arterial device may include insertion through a skin of a face of the subject. Inserting the second arterial device into a terminal branch of the OA of the subject may include insertion within at least one of a SOA, STA, a dorsal nasal artery (DNA), or a facial artery (FA) of the subject.

In some examples, the method of inducing retrograde blood flow may include fluidly coupling a first device located within an arterial system of a subject with a second device located within a venous system of the subject. The method may further include inducing a first flow of blood from an OA of the subject, through the first device, through the second device, and into the venous system of the subject. The method may include inducing a second flow of blood through the first device, through a third device located in a terminal branch of the OA of the subject, and into the arterial system of the subject.

Examples of the method may include any one or more of the following features. The method may include treating at least one of the OA or a junction between the ICA and the OA of the subject. The first device may include an expandable portion on a distal end thereof and the method may further include expanding the expandable portion to impede antegrade blood flow in at least a portion of the arterial system of the subject. The method may include compressing an arterial wall of the arterial system against a surface of the first device. The method may include inserting the first device within the arterial system of the subject via a cervical approach. The method may include inserting the third device in at least one of a SOA, a STA, a DNA, or a FA of the subject.

The present disclosure also includes a medical system that may include a first arterial sheath including an expandable occlusion device on a distal end thereof and a second arterial sheath configured for insertion into a terminal branch of an OA of a subject. The system may further include a venous sheath and a stopcock. Each of the first arterial sheath, second arterial sheath, and venous sheath may be coupled to the stopcock.

Examples of the system may further include any one or more of the following features. The expandable occlusion device may be a balloon configured to engage a wall of at least one of a CCA or the ICA of the subject. A first conduit may extend between the stopcock and the venous sheath, and a second conduit may extend between the stopcock and the second arterial sheath. A filter may be positioned along the first conduit between the stopcock and the venous sheath. The second arterial sheath may be configured for insertion within at least one of a SOA, a STA, a DNA, or a FA of the subject.

The present disclosure also includes a system for treating an eye disease, disorder, or condition that may include restoring or increasing an amount of blood flow to an eye, an eye portion, or a structure associated with the eye or portion of the eye of a subject. The system may include a transcutaneous intervention device adapted and configured for ocufacial access and entry into vasculature between an ICA of the eye.

The present disclosure also includes methods, devices, and systems for removing a blockage in the ostium or a proximal segment of the OA near the ICA. In these embodiments, removing the blockage comprises opening a channel or access through the ostium sufficient to provide a therapeutically beneficial result to the eye, the rear of the eye, or portions thereof. The present disclosure also includes restoring and/or improving blood flow anywhere in the vascular pathway to or within the eye.

The present disclosure also involves restoring or improving blood flow to the eye, thereby altering the complement system. In some embodiments of the disclosure, several CS factors, their activators, and complement regulatory proteins where identified as cardinal constituents of drusen, the hallmark extracellular retinal deposits associated with early AMD. In other embodiments of the disclosure, restoring or improving blood flow reduces or mediates the abnormal concentration of primary complement factors and their activated products in the vasculature of patients suffering from eye diseases such as AMD and glaucoma.

In some examples of the present disclosure, restoring or improving blood flow to the back of the eye may eliminate, reduce, or mediate CS activation, which directly damages host tissue and recruits immune cells to the vicinity of an active complement cascade. In other examples, the choroid- and retinal pigment epithelium-based regulation of the CS activity has been found to play an important role in the functions of the eye.

The present disclosure is also directed to devices and methods for percutaneous access and treatment of vascular structures in the rear of the eye, including treatment for the symptoms related to Wet Age Related Macular Degeneration (WAMD) by removal of stenosis of the OA, thereby restoring normal, or near normal, blood flow to the rear of the eye, including the retina and associated structures. The present disclosure is also related to methods and devices for selective manipulation of intra ocular pressure (IOP) be means of mechanical force for the purpose of inducing retrograde flow in the ophthalmic vasculature.

The present disclosure describes an apparatus for treating obstruction of the OA, comprising an IOP device for mechanically applying a force against the front of the eye to increase IOP sufficient to temporarily stop antegrade blood flow in the ophthalmic vasculature at the back of the eye and thereby induce retrograde flow in the ophthalmic vasculature; an atherectomy kit for performing an atherectomy upon the OA of a patient in need thereof; and a debris capture device for placement within the ophthalmic vasculature to capture atherectomy debris.

In another example, the present disclosure describes a device using mechanical force selected from the group consisting of hydraulic force, pneumatic force, gravitational force, spring force, and user-applied force, to contact the anterior portion of the eye(s) for the purpose of IOP manipulation, and wherein the apparatus is configured for use on one eye or on both eyes simultaneously.

In another example, the apparatus may use mechanical force applied to the anterior portion either directly or through the closed eyelid.

In another example, the apparatus may contain the capability to measure the IOP.

In another example, the apparatus may measure the IOP using a sensor implanted within the vitreous cavity that is capable of assessing IOP values and transmitting data wirelessly.

In another example, the wireless data transmission may be provided in a continuous and real time manner.

In another example, the IOP may be measured with a sensor temporarily placed within the vitreous cavity via a wired or wireless manner.

In another example, a feedback mechanism may be provided for receiving IOP values (data) and providing monitoring capability.

In another example, a feedback mechanism may be provided for the general control of the IOP manipulation such that the IOP may be increased or decreased as deemed necessary.

In another example, a feedback mechanism may be combined with a control function that allows for the ability to control the rate of increase and/or decrease of IOP as deemed necessary.

In another example, a feedback mechanism may be combined with a control function such that the IOP values may be increased, decreased, maintained, or cycled as necessary.

In another example, a feedback mechanism may be combined with a control function such that the rate of IOP increase, decrease, or steady state may be controlled.

In another example, a feedback mechanism may be combined with a control function such that specific parameters related to IOP values, rates of force, and time at force may be specified and controlled.

In another example, a feedback mechanism may be combined with a control function such that when specific parameters are not met, the user is informed.

In another example, a feedback mechanism may be combined with a control function such that information related to the IOP value is displayed for the user to see.

In another example, a feedback mechanism may be combined with a control function such that the data may be displayed, manipulated, and/or captured in a method for record keeping.

The present disclosure also includes a method of treating obstruction of the OA, comprising the steps of inducing retrograde flow in the ophthalmic vasculature by applying a mechanical force against the front of the eye to increase IOP sufficient to temporarily stop antegrade blood flow in the ophthalmic vasculature at the back of the eye; performing an atherectomy upon the OA of a patient in need thereof during retrograde blood flow; and deploying a debris capture device within the ophthalmic vasculature to capture atherectomy debris, wherein the retrograde flow blocks the debris from the atherectomy from flowing downstream and causing an ischemic event.

In another example, there is provided wherein the retinal arteries may flow in reverse for a predetermined timeframe.

In another example, there is provided wherein intravascular debris within the retinal artery may flow in reverse for a predetermined amount of time.

In another example, there is provided wherein the ophthalmic arteries may flow in reverse for a predetermined timeframe.

In another example, there is provided wherein intravascular debris within the OA may flow in reverse for a predetermined amount of time.

In another example, there is provided use in conjunction with an interventional device placed within the target anatomy for the purpose of tissue removal e.g., stenosis, lesions, etc.

In another example, there is provided wherein debris is captured by placement of a capture device placed within the target anatomy.

In another example, there is provided a tissue removal device for treating obstruction of the OA, comprising: a percutaneously delivered tapered corewire ranging in diameter from about 0.19 mm to about 0.88 mm, the corewire disposed within a delivery sheath, said corewire having a tissue cutting element at or near a distal end, said corewire having an integral inflatable balloon section at the distal end as a protective element, and said corewire having an atraumatic tip.

In another example, the device may be configured for percutaneous access of the ICA.

In another example, the device may be configured for percutaneous access of the OA.

In another example, the device may be configured to be visible using non-invasive imaging techniques (e.g., fluoroscopy).

In another example, the device may include distal emboli protection.

In another example, there is provided a flow direction device to aid in the positioning of the device within the target anatomy.

In another example, there is provided a flow direction device that may use reverse flow to aid in the removal of the device from within the target anatomy during selectively induced retrograde flow.

In another example, there is provided a specifically shaped guidewire to access the OA from the ICA.

In another example, there is provided a specifically designed guiding catheter to access the OA from the ICA.

In another example, there is provided a specifically shaped guidewire to access the OA from the ICA, through the guiding catheter, once the guiding catheter has transited the OA, wherein this guidewire is configured to gain further downstream OA access without disturbance of vessel physiology due to guidewire tip shape.

In another example, there is provided a downstream protection element for downstream protection in the ICA.

In another example, a method of the present disclosure may use a shaped tip guidewire, a straight tip guidewire, and a guiding catheter, comprising the steps in which the straight tip guidewire is used alone, or in conjunction with the guiding catheter to access the OA from the ICA, wherein once the OA has been cannulated, the shaped tip guidewire is exchanged for the straight tip guidewire for the balance of the procedure. Further, once the OA has been cannulated, the shaped tip guidewire is exchanged with an interventional device for the balance of the procedure.

In another example, there is provided an apparatus for capturing atherectomy debris as it is removed, comprising a single hypotube cut to contain a combination atherectomy device and distal protection device.

In another example, the atherectomy device portion may fit within a delivery sheath such that the fully expanded diameter is achieved when the device is moved out of sheath and into the target anatomy with the fully expanded diameter at 1.4 mm, with compliance to a vessel as small as 0.7 mm.

In another example, the atherectomy device portion may fit within a delivery sheath and the fully expanded diameter is achieved when the device is moved out of sheath, into the target anatomy and a central, slideable corewire is manipulated to achieve the final diameter.

In another example, the apparatus may be constructed of a solid corewire with a mounted atherectomy and distal protection device.

In another example, the solid corewire may contain external geometry specific to the function of performing atherectomy work.

In another example, the atherectomy portion of the apparatus may be expandable.

In another example, the atherectomy portion of the apparatus may be non-expandable.

In another example, the atherectomy portion of the apparatus may be non-expandable, but rotatable such that rotation induces a diametric increase in the apparatus.

In another example, the atherectomy device may fit within a delivery sheath such that the fully expanded diameter is achieved when the device is moved out of sheath and into the target anatomy.

In another example, the atherectomy device portion may fit within a delivery sheath such that the non expanded diameter is revealed when the device is moved out of sheath and into the target anatomy.

In another example, the apparatus may be constructed of a balloon designed to inflate such that contact with the target anatomy is achieved.

In another example, the balloon may have external materials affixed directly to the balloon surface to facilitate atherectomy.

In another example, the balloon may have external emboli protection.

In another example, the balloon may be mounted on a polymer catheter typical of current vascular procedure technology.

In another example, the balloon may be mounted on a solid corewire.

In another example, the balloon may be mounted on a hypotube.

In another example, there is provided a device for the removal of debris by aspiration.

In another example, the apparatus may have a deployed, fully expanded diameter of 1.2 mm to 1.4 mm, compressible yet effective at 0.7 mm of deployed diameter.

In another example, the apparatus may have a deployed, fully expanded diameter of 1.0 mm to 1.6 mm, compressible yet effective at 0.7 mm of deployed diameter.

In another example, the apparatus may have a balloon shape optimized to affect removal of material.

In another example, the apparatus may have an aspiration device for removal of debris by aspiration via an external sheath.

In another example, the apparatus may be made of materials selected from nitinol, stainless steel, or other materials commonly associated with intravascular medical devices.

In another example, the method may include the apparatus being percutaneously inserted via the ICA and navigated to the OA.

In another example, the navigation of the apparatus may be guided by use of a non-invasive imaging methodology (e.g., fluoroscopy).

In another example, distal protection may be provided for the ICA.

In another example, distal protection may be provided for the OA.

In another example, there is provided a method wherein removal of debris by aspiration is provided for while in the OA.

In another example, there is provided a method for providing treatment for the symptoms related to WAMD, comprising the step of removal of stenosis of the OA, thereby restoring normal, or near normal, blood flow to the rear of the eye, including the retina and associated structures.

In another example, there is provided a method for providing a pharmaceutical based treatment for the symptoms of WAMD by delivery of a pharmaceutical compound(s) specifically targeted for the treatment of WAMD.

In another example, there is provided a method for providing a pharmaceutical treatment for the medication and/or restenosis of a specific section of the OA by delivery of a pharmaceutical compound(s) specifically targeted for the treatment of vascular lesions.

In another example, there is provided a method for providing a pharmaceutical treatment for the prevention and/or treatment of thrombus or thrombus related conditions in a specific section of the OA by delivery of a pharmaceutical compound(s) specifically targeted for the treatment of thrombus or thrombus related conditions.

In another example, there is provided an apparatus for providing a pharmaceutical based treatment for the symptoms of WAMD by physical delivery of a pharmaceutical compound(s) specifically targeted for the treatment of WAMD.

In another example, there is provided an apparatus for providing a pharmaceutical treatment for the medication and/or restenosis of a specific section of the OA by physical delivery of a pharmaceutical compound(s) specifically targeted for the treatment of vascular lesions.

In another example, there is provided an apparatus for providing a pharmaceutical treatment for the prevention and/or treatment of thrombus or thrombus related conditions in a specific section of the OA by physical delivery of a pharmaceutical compound(s) specifically targeted for the treatment of thrombus or thrombus related conditions.

In another example, the apparatus may be packaged within a single unit, containing a hybrid catheter and flow directed balloon.

In another example, there is provided an apparatus wherein the OD of single unit being 6-9 French at the thicker, proximal end of the hybrid catheter/balloon with the distal 2-5 cm of the apparatus being 0.12 mm to 0.19 mm in diameter of a flow directed guidewire with the final distal portion of the apparatus being 8 mm to 15 mm of the apparatus being a flow directed balloon.

In another example, there is provided an apparatus wherein the flow directed balloon inflates from a minimum of 0.7 mm to a maximum of 1.4 mm.

In another example, the apparatus may coat the balloon with a drug for delivery and compression into the wall of the arterial source with the stenotic lesion.

BRIEF DESCRIPTION OF THE DRAWINGS

FIGS. 11A and 11B illustrate exemplary before and after side views of an embodiment of the present disclosure.

FIGS. 15A and 15B illustrate exemplary before and after side views of an embodiment of the present disclosure.

DETAILED DESCRIPTION

Figure 1:
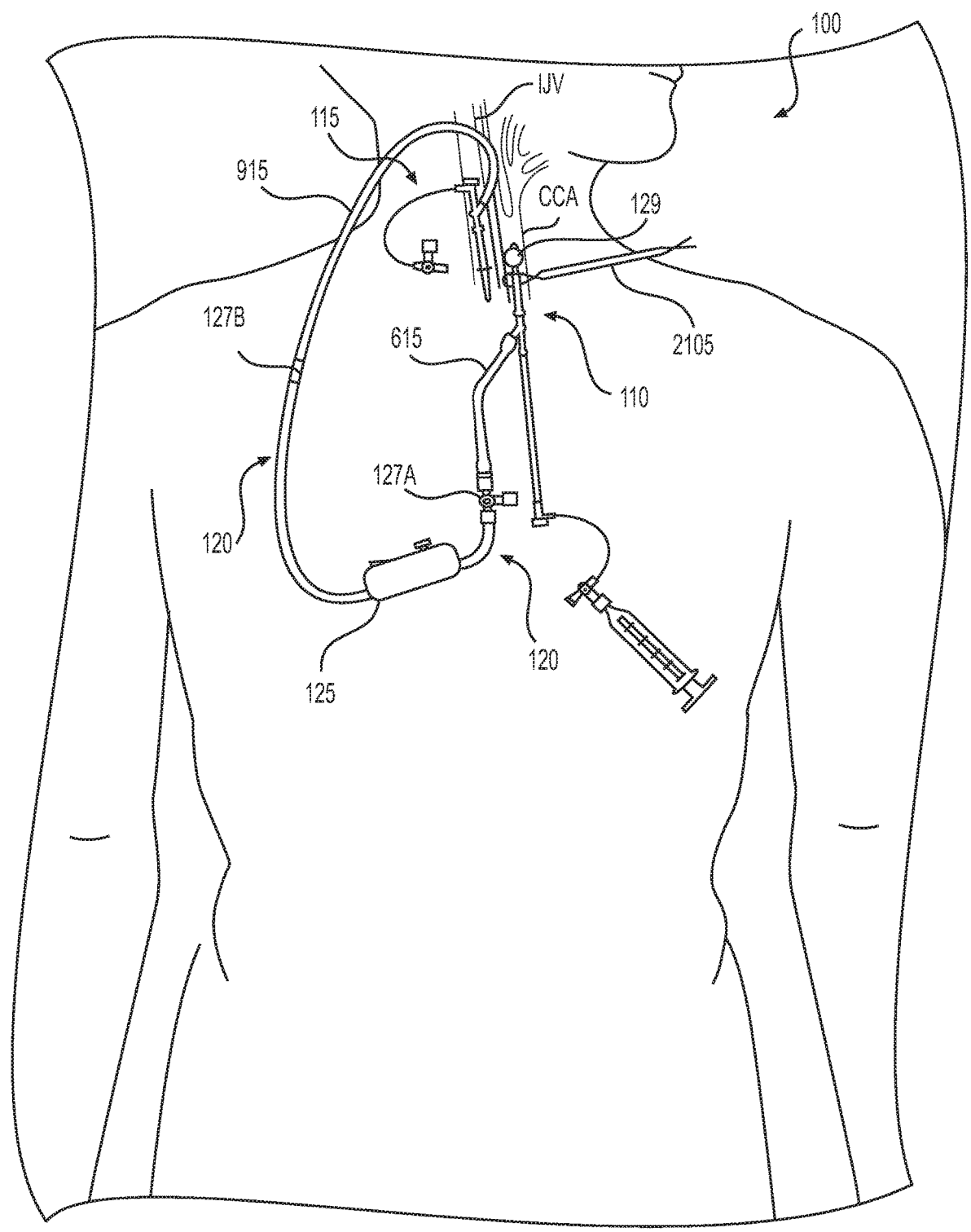
FIG. 1 illustrates an exemplary system of devices for transcervical OA procedures using a retrograde blood flow embolic protection system, wherein an arterial access device accesses the OA via a transcervical approach and a venous return device communicates with the IJV, according to an aspect of the present disclosure.

Both the foregoing general description and the following detailed description are exemplary and explanatory only and are not restrictive of the features, as claimed.

The singular forms "a," "an," and "the" include plural reference unless the context dictates otherwise. The terms "approximately" and "about" refer to being nearly the same as a referenced number or value. As used herein, the terms "approximately," "about," and "substantially," generally should be understood to encompass ±5% of a specified amount or value, unless otherwise stated.

As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

The terms "proximal" and "distal" are used herein to refer to the relative positions of the components of an exemplary medical device or insertion device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body.

The terms "downstream" or "antegrade" and "upstream" or "retrograde," when used herein in relation to the subject's vasculature, refer respectively, to the direction of blood flow and the direction opposite that of blood flow, respectively. In the arterial system, "downstream" or "antegrade" refers to the direction further from the heart, while "upstream" or "retrograde" refers to the direction closer to the heart.

As used herein, "embolic debris" means any biologic or non-biologic mass, the presence of which in the vasculature may present a risk, including, but not limited to, plaque, emboli, etc.

"Nutrients" as used herein includes, but is not limited to, oxygen, hemoglobin, complement, and glucose.

As used herein, "therapeutically beneficial result" refers to any perceived or actual benefit to the patient. Examples of beneficial results include, but are not limited to, treatment of an eye disease, condition, and/or symptom; restoring or increasing blood flow in any manner that treats an eye disease, condition, and/or symptom; and removing or partially removing a blockage in the blood flow path between the heart and the eye, preferably in the OA or a portion thereof.

In this disclosure, "reverse flow, "retrograde flow," and "retrograde blood flow" are used synonymously. As used herein, reverse flow or retrograde flow is the flow of blood opposite to the direction of blood flow under normal blood flow conditions, and refers to the consequences of blocking blood flow in an artery and establishing a fluid flow connection with a vein. Under these conditions, the natural pressure gradient differential causes blood to flow in a reverse direction in the artery. For example, when flow through the ICA is blocked, the natural pressure gradient between the ICA and the venous system causes blood to flow in a retrograde or reverse direction from the vasculature of the eye, through the OA, and through the ICA. Reverse flow may be achieved by creating a pressure gradient so blood flow is reversed and directed, for example, from the treatment site into a lumen of a catheter to be rerouted to another location. The pressure gradient can be facilitated by creating a low-pressure source(s), which can be within the catheter itself or created in a desired location within the vasculature that is in fluid communication with the lumen of the catheter.

In a reverse flow embolic protection method, an arterial access cannula may be connected to a venous cannula in order to establish a reverse or retrograde flow from an artery (such as the ICA and/or OA) through the arterial cannula and away from the eye and/or vasculature of the eye. Flow in an artery is occluded, typically by inflating a balloon on the distal tip of the cannula, in a carotid artery, the ICA, or the OA, thereby reversing blood flow in the ICA and/or the OA. After such reverse or retrograde flow is established, any catheter or interventional procedure in the OA can be performed with a greatly reduced risk of emboli entering the eye.

As used herein, "blockage" refers to complete or partial blockage; reduced, restricted, or eliminated blood flow; sometimes caused by plaque, tortuous shaped anatomy, vessel failure, or dysfunction. Without intending to be bound by theory, it is believed that any blockage or reduction in fluid or blood flow is a mediator of certain consequences described more particularly below, and that any condition, such as a blockage, that leads to lowered nutrient availability and/or consumption is a direct mediator of normal physiologic function. It is also believed that those conditions also mediate metabolic waste removal from cells, organs, and other biological structures.

In accordance with this disclosure, possible eye diseases or conditions include, but are not limited to, one or more of the following: reduced or blocked blood flow in one or more arteries or system of arteries; reduced or blocked source of energy or nutrients to a cell, organelle of a cell, mitochondrion, group of cells, or organ; altered aerobic energy metabolism; altered mitochondria oxidative phosphorylation; decreased or blocked supply of glucose; altered aerobic energy metabolism; photoreceptor dysfunction and degeneration; altered energy homeostasis; glucose; glucose and oxygen; mitochondrial damage; one or more combinations of substrates, including, but not limited to, glucose, pyruvate, lactate, L-glutamine, and β-hydroxybutyrate; altered mitochondria oxidative phosphorylation; complement; any molecule in the complement cascade; and localized drug and/or an oxygen device for increasing flow or amount of oxygen in one or more eye tissues; decreased hemoglobin amount or delivery to one or more intra-cranial structures or to one or more eye tissues; reduced or blocked blood flow or rate anywhere in the fluid flow path between the ICA and eye tissue; and any blockage or partial blockage in one or more arteries or system of arteries; any mediation of the complement system, the complement cascade, and/or one of the complement cascade associated molecules; and lowered/blocked nutrient supply and/or metabolic waste removal is implicated, and therefore may mediate one or more diseases, disorders, or biological function.

These conditions may occur in one or more of the following areas or structures, including, but not limited to: one or more arteries; one or more cranial arteries; one or more arteries associated with supplying blood flow to the eye; the ICA; the OA; anywhere in the fluid flow path between the ICA and eye tissue; the junction between the ICA and the OA, which is referred to in this disclosure as the ostium; and secondary areas of the anatomy, which include the vascular system commonly referred to as the terminal branches. These secondary areas include, but are not limited to the SOA, the STA, the DNA, the FA; any cranial artery; and in any of the junctions or ostia between any of the vasculature between the ICA and one or more eye tissues.

Examples of eye diseases and conditions include, but are not limited to: AMD (both dry and wet); neuronal cell death; Alzheimer's disease; dementia; glaucoma; diabetic macula edema; macular telangiectasia (e.g., type 1 or 2 macular telangiectasia); atrophic macular degeneration; chorioretinopathy (e.g., central serous chorioretinopathy); retinal inflammatory vasculopathy; pathological retinal angiogenesis; age-related maculopathy; retinoblastoma; Pseudoxanthoma elasticum; a vitreoretinal disease; choroidal sub-retinal neovascularization; central serous chorioretinopathy; ischemic retinopathy; hypertensive retinopathy or diabetic retinopathy (e.g., nonproliferative or proliferative diabetic retinopathy, such as macular edema or macular ischemia); retinopathy of prematurity (e.g., associated with abnormal growth of blood vessels in the vascular bed supporting the developing retina); venous occlusive disease (e.g., a retinal vein occlusion, branch retinal vein occlusion or central retinal vein occlusion); arterial occlusive disease (e.g., branch retinal artery occlusion (BRAO); central retinal artery occlusion or ocular ischemic syndrome); central serous chorioretinopathy (CSC); cystoid macular edema (CME) (e.g., affecting the central retina or macula, or after cataract surgery); retinal telangiectasia (e.g., characterized by dilation and tortuosity of retinal vessels and formation of multiple aneurysms, idiopathic JXT, Leber's miliary aneurysms, or Coats' disease); arterial macroaneurysm; retinal angiomatosis; radiation-induced retinopathy (RIRP); or rubeosis iridis (e.g., associated with the formation of neovascular glaucoma, diabetic retinopathy, central retinal vein occlusion, ocular ischemic syndrome, or chronic retinal detachment); distortions and/or blind spots (scotoma); changes in dark adaptation (diagnostic of rod cell health); changes in color interpretation (diagnostic of cone cell health); decrease in visual acuity; and cataracts (e.g., age-related cataract).

In a general sense, the pathogenesis of some of these eye diseases is similar if not the same as those seen for cardiac diseases and for abdominal aorta conditions. However, the anatomy of the vasculature behind the eye is typically smaller, includes more branches, and includes more sharp angles in the blood flow pathway. Further, the vascular system supplying blood to the eye is closer to the brain; any uncaptured or non-rerouted debris may cause an immediate stroke.

The use of catheter delivery systems for positioning and deploying therapeutic devices, such as balloons, stents, and embolic devices, in the vasculature of the human body has become a standard procedure for treating endovascular diseases. It has been found that such devices are particularly useful as an alternative in treating areas where traditional operational procedures are impossible or pose a great risk to the patient. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

The present disclosure describes an apparatus, system, and method of treatment of eye disease using any apparatus or system that involves reverse blood flow or retrograde blood flow. More specifically, the present disclosure also describes apparatus, systems, and methods for inducing reverse blood flow or retrograde blood flow in one or more arteries, including, but not limited to, the OA.

In some embodiments of the present disclosure, retrograde blood flow may be established between an artery and a vein. In other embodiments, a reverse flow or retrograde system may be established in any location suitable for treatment of eye disease. Exemplary locations include, but are not limited to, the ICA, the external carotid artery (ECA), the CCA, the SOA, the STA, the OA, and an appropriate site in the venous system, which includes, but is not limited to, the IJV or the femoral vein.

In other embodiments, retrograde flow is used in combination with other medical procedures and devices to access, treat, and/or deploy a medical device in the fluid flow path between the ICA and the eye. As used herein, fluid flow path refers to a section of the ICA, the ostium, the OA, and other arteries that supply blood to the eye.

A reverse flow system may be variously configured and include a wide number of elements and devices. The typical reverse flow system includes an access device or port into an artery, an access device or port into a vein, one or more tubes or conduits connecting the two access ports, and an occlusion device (e.g., balloon or clamp or the like).

Exemplary reverse and/or retrograde blood flow devices and systems include, but are not limited to, U.S. Pat. Nos. 9,259,215; 9,241,699; 9,265,512; 8,545,432; 7,927,347; 7,235,095; 6,936,060; 6,929,634; 6,908,474; 6,905,490; 6,902,540; 6,855,162; 6,827,726; 6,824,558; 6,645,222; 6,641,573; 6,540,712; 6,423,032; 6,413,235; 6,344,054; 6,336,933; 6,302,908; 5,820,595; 5,709,701; and U.S. Patent Application Nos. 2009/0024072 and 2011/0160762; all of which are incorporated by reference herein in their entireties.

In some embodiments of the present disclosure, eye disease may be treated using at least one arterial access device and a retrograde flow system, using a percutaneous transfemoral approach, a transcervical approach, cervical access, or combinations thereof. The other embodiments, the arterial access device and retrograde flow system may use a femoral or cervical approach.

In order to reverse blood flow in the CCA during interventional procedures, creation of a circuit is necessary to extract blood from the CCA and return it to a venous location. Extracting blood from the CCA and returning it to a venous location takes advantage of compensatory blood flow through the circle of Willis (COW), high pressure of the arterial system, and low pressure of the venous system. Reversing blood flow allows for filtration of the blood so that particulates generated during an interventional procedure are removed from circulation thereby preventing/reducing the possibility of an embolic event. Several structures are typically required to create the reverse blood flow circuit: 1) an artery sheath which provides access to the artery; 2) an arterial occlusion device, typically catheter based, which is inserted into the artery via the sheath. In some examples of the present disclosure, the device may incorporate a distal inflatable element, typically similar in design to an angioplasty balloon, which is designed to be positioned into the artery and inflated. The balloon is dimensionally designed to occlude the artery such that normal antegrade blood flow will be stopped upon full inflation and forced through one of the device lumens during the reverse flow portion of the procedure. In other embodiments of the present disclosure, the device may have one or more thru lumens capable of carrying blood and inserting medical instruments as well as a port (stopcock) for accessing these lumens and connecting to a venous entry for returning the blood. 3) A venous sheath. This sheath provides access to the venous system and may include a port (stopcock) for connecting to the circuit to serve as the return point for the arterial blood. 4) A blood filter. This filter is designed with micropores that filter out particulate, but allow blood to flow from one side to the other. This filter may have lure connecters on each end to allow for connection to the reverse flow circuit. 5) IV lines. These lines connect the occlusion device port (stopcock) to the filter and the filter to the venous sheath port (stopcock).

The present disclosure includes methods that may include, but are not limited to, inserting and/or delivering an arterial access device to a desired artery and position, blocking flow in the artery, and allowing retrograde or reverse flow to cause blood to flow in a reverse or retrograde flow direction and into a shunt. The retrograde blood flow may then be directed through the venous return device into a vein.

Some embodiments may include high flow capacity, one aspect of which may be a delivery apparatus having a large bore. In other embodiments, the large bore may include a large internal dimension, useful for example, in delivering and using certain transcatheter devices.

In some examples of the present disclosure, lumen size for the system (circuit) components (including catheters, sheaths, stopcocks, and filters) may be optimized for a particular location and/or circuit. Average CCA diameters can be in the 6.0 mm/18 Fr (or larger) range and average IJV diameters can be in the 13 mm/34 Fr (or larger) range. Larger than 2.66 mm/Fr 8 may also be used to accommodate these artery/vein sizes.

Without intending to be bound by theory, it is believed that pore size of one or more filters may be optimized and/or coordinated in order to achieve medically appropriate filtration. In accordance with some embodiments of the present disclosure, the system may include one or more filters. In systems having more than one filter, the pore size of the filters may be the same or different.

According to some embodiments of the present disclosure, the circuit may be optimized for length. Without intending to be bound by theory, it is believed that carotid access may be beneficial, in part because of a circuit in which the guidewire may be approximately 15 inches in length.

In some embodiments of the present disclosure, the reverse flow system is used to access or treat an arterial area or segment between the ICA and the eye. Such treatment includes, but is not limited to, removing a blockage. In some embodiments, the treatment may include restoring or increasing blood flow to the eye. In other embodiments, the treatment, apparatus, or system, removes a blockage or constriction in the OA near the ICA, e.g., in the ostium and/or in the first section of the OA before the sharp bend in the artery.

Restoring and/or increasing blood flow is used herein to refer to any device, method, therapy, or combination that changes the blood flow to the eye. Examples of such include, but are not limited to, increasing the blood flow anywhere in the vasculature leading to the eye or a portion of the eye; removing or opening an obstruction in the fluid flow path in the vasculature leading to the eye, e.g., from the ICA through the OA; delivering and deploying a stent in the fluid flow path in the vasculature leading to the eye; using atherectomy or similar devices to physically remove portions of any obstructions in the vasculature leading to the eye or portion of the eye; and localized drug and/or an oxygen device for increasing flow or amount of oxygen in one or more eye tissues. In some embodiments of the present disclosure, the device or method may be combined with a known or new drug or oxygen device in order to treat one or more eye diseases or conditions.

The present disclosure also includes restoring and/or increasing the amount of nutrients that is available to one or more parts of the eye or to the eye area, specifically by removing or partially opening a blockage in one or more of the arteries that supplies blood flow to the eye. In some embodiments of the disclosure, a blockage is removed or opened in the ICA, the OA, the ostium (as used herein, referring to the junction between the ICA and the OA), or combinations thereof. To or near the eye, as used herein, refers to the vasculature system that supplies blood to the various structures of the eye. As noted above, nutrients as used herein include but are not limited to oxygen, hemoglobin, complement, and glucose.

The present disclosure also includes methods, devices, and systems for removing a blockage in the ostium or a proximal segment of the OA near the ICA. In these embodiments, removing the blockage comprises opening a channel or access through the ostium sufficient to provide a therapeutically beneficial result to the eye, the rear of the eye, or portions thereof. The present disclosure also includes restoring and/or improving blood flow anywhere in the vascular pathway to or within the eye.

The present disclosure should not be limited solely to changing vascular flow in order to improve or restore the amount of nutrients that are delivered to the eye. For example, in some embodiments, the vascular flow may be unaffected for the most part, but the amount or concentration of nutrients may be increased, thereby increasing the amount of nutrients that may be delivered to the eye or associated with the eye. One skilled in the art may recognize, with the teaching of this disclosure, that there are other biological systems or capabilities that may be used to increase the amount of nutrients that are delivered to the eye.

In other embodiments of the disclosure, reducing blockage includes, but is not limited to, piercing or penetrating the blockage. In other embodiments, piercing and penetrating the blockage refers to obtaining sufficient blood and/or fluid flow through or around the blocked vascular area sufficient to provide a therapeutically beneficial amount of oxygen to the eye or a portion of the eye.

Some embodiments of the present disclosure include a retrograde flow system that does not require the use of a balloon or the like. In these balloonless systems, methods, and assemblies, the flow direction element may be an external force applied to an artery to compress the artery around the sheath. As used herein, external force refers to any element or structure that functions to apply force, to clamp or close the artery against the sheath. Exemplary elements include, but are not limited to a clamp, vise, band, suture, pincer, contractor, constrictor, and the like. In function, any such element compresses or closes the artery against the sheath or tube, thereby forcing any blood flow through the lumen of the tube rather than around the tube.

The present disclosure includes methods and devices for treating a non-human animal. Some embodiments include treating a dog, including, but not limited to, treating central serous retinopathy.

In accordance with the present disclosure, a reverse flow system may be variously configured and include a variety of elements and components. Typical components and elements include, but are not limited to, an arterial access device; a venous return device; one or more shunts; a flow control assembly; an arterial port; a venous port; a shunt valve; a flush line; one or more shut off valves; one or more connectors; one or more tubing members; one or more syringes; one or more vessel closure devices; one or more suture delivery devices; one or more interventional catheters; one or more interventional delivery devices; one or more external receptacles; one or more adapters; one or more Y connectors; a flow state indicator; a flow rate activator; one or more sensors; a timer; contrast; one or more stopcocks; or one or more manifolds.

The present disclosure also includes a delivery system configured or adapted to position and/or orient a medical device in the OA; atherectomy or angioplasty in the OA; all in combination with a reverse flow system.

Referring to FIG. 1, according to an embodiment of the present disclosure, the retrograde flow system 100 can include the arterial access device 110, venous return device 115, and shunt 120 which provides a passageway for retrograde flow from the arterial access device 110 to the venous return device 115. The system 100 may also include the flow control assembly 125, which interacts with the shunt 120 to regulate and/or monitor retrograde blood flow through the shunt 120.

FIG. 1 shows an exemplary embodiment of a retrograde flow system 100 that is adapted to establish and facilitate retrograde or reverse flow blood circulation in the OA in order to limit or prevent the release of emboli into the eye. The system 100 interacts with the OA to provide retrograde flow from the vasculature of the eye to a venous return site, such as the IJV (or to another return site such as another large vein or an external receptacle in alternate embodiments). The retrograde flow system 100 may include an arterial access device 110, a venous return device 115, and a shunt 120 that provides a passageway for retrograde flow from the arterial access device 110 to the venous return device 115.

An optional flow control assembly 125 can interact with the shunt 120. The flow control assembly 125 can be adapted to regulate and/or monitor the retrograde flow from the OA to the IJV. Optionally, the flow control assembly can be replaced with or used in conjunction with an in-line filter. The flow control assembly 125 can interact with the flow pathway through the shunt 120, either external to the flow path, inside the flow path, or both.

The illustrated embodiment shows occluding the CCA. In another embodiment, the occlusion element is positioned in and occludes the ICA and/or the OA.

In an embodiment of the present disclosure, the arterial access device 110 at least partially inserts into the ICA and/or the OA and the venous return device 115 at least partially inserts into a venous return site such as the IJV. The arterial access device 110 and the venous return device 115 couple to the shunt 120 at connection locations 127a and 127b. When flow through the ICA is blocked, the natural pressure gradient between the ICA and the venous system can cause blood to flow in a retrograde or reverse direction from the eye vasculature through the OA and the ICA, and through the shunt 120 into the venous system. The flow control assembly 125 can modulate, augment, assist, monitor, and/or otherwise regulate the retrograde blood flow.

In an alternative embodiment, the flow control assembly may be replaced with an inline blood filter; or the flow control assembly may be used in combination with an inline blood filter.

In the exemplary embodiment of FIG. 1, the arterial access device 110 can access the CCA via a transcervical approach. Transcervical access provides a short length and non-tortuous pathway from the vascular access point to the target treatment site thereby easing the time and difficulty of the procedure, compared for example to a transfemoral approach. Additionally, this access route reduces the risk of emboli generation from navigation of diseased, angulated, or tortuous ICA or OA anatomy. At least a portion of the venous return device 115 can be placed in the IJV. In another embodiment, transcervical access to the OA is achieved percutaneously via an incision or puncture in the skin through which the arterial access device 110 is inserted. An occlusion element 129, such as an expandable balloon, can be used to occlude the ICA or OA at a location proximal of the distal end of the arterial access device 110. The occlusion element 129 can be located on the arterial access device 110 or it can be located on a separate device. In an alternate embodiment, the arterial access device 110 accesses the ICA and the OA via a direct surgical transcervical approach. In the surgical approach, the OA can be occluded using a tourniquet 2105. The tourniquet 2105 is shown in phantom to indicate that it is a device that is used in the optional surgical approach.

Some embodiments of the present disclosure include an arterial access device adapted and configured for use only with an interventional reverse flow system. In these embodiments, there is no need for a vascular surgeon or cut-down procedure. In devices, methods, and systems according to this embodiment, a neuroradiologist or interventionalist is required to perform the procedure.

Figure 2:
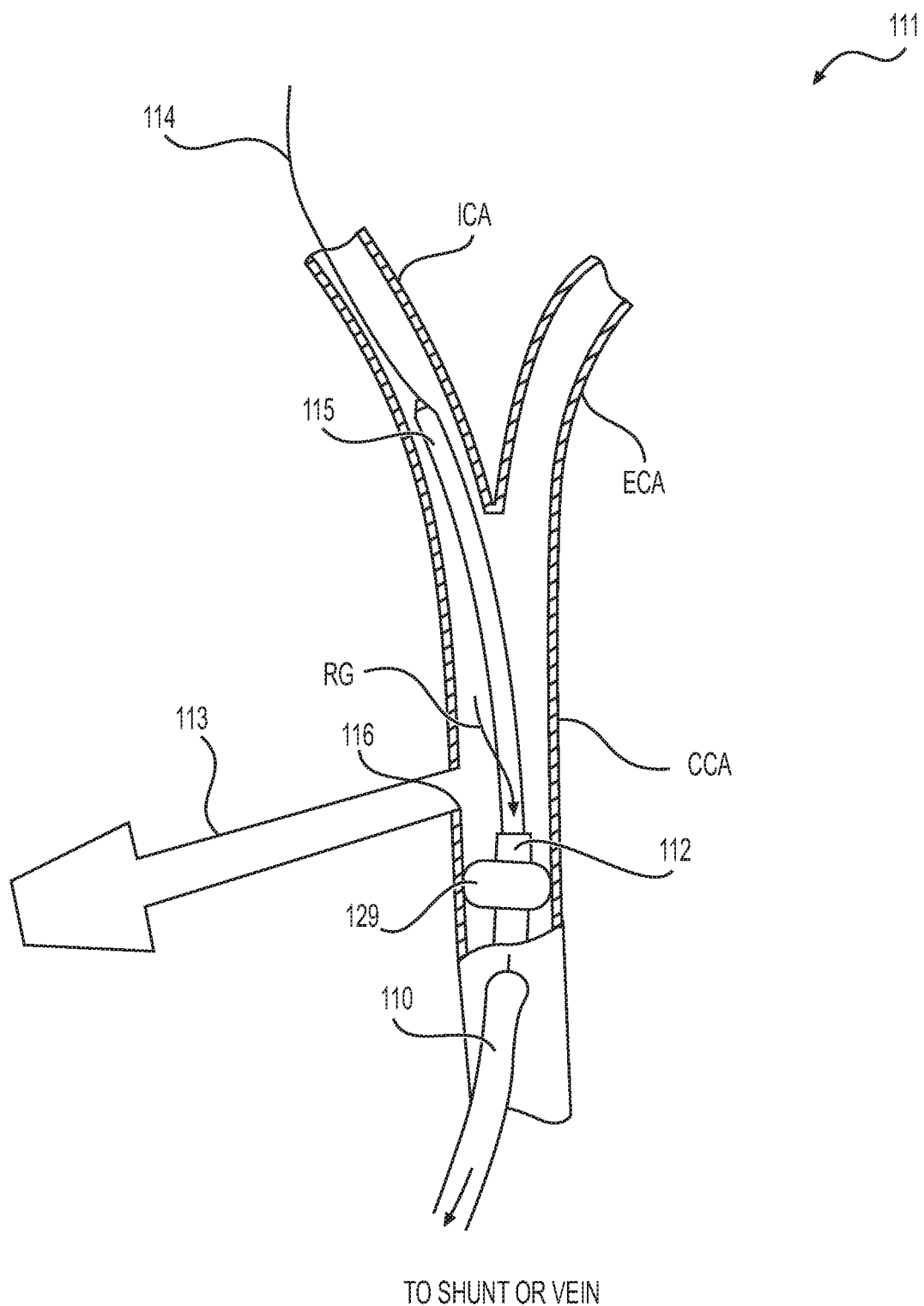
FIG. 2 illustrates an embodiment of an arterial access device, according to an aspect of the present disclosure.

In another embodiment of the present disclosure, an example of which is shown in FIG. 2, the arterial access device or system 111 includes a device delivery system 115, which may include an occlusion element 129, such as a balloon or expandable member, to block the blood flow; a conduit 112 or catheter having a lumen through which retrograde blood may pass; and a guidewire 114. The access device or system 111 may also include a sheath 113 having a distal end 116 configured to be flush with the internal wall of the artery and located in a position near but above the occlusion element 129.

In the illustrated embodiment, the sheath accesses the artery through a skin puncture in the neck (not a surgical cut-down), and the catheter accesses the artery through a cut-down procedure. In another embodiment, the sheath accesses the artery through a skin stick in the neck and the interventional catheter accesses the artery through a femoral access in the groin.

In other embodiments of the arterial access device, the sheath is adapted to be introduced through an incision or puncture in a wall of a CCA, either an open surgical incision or a percutaneous puncture established, for example, using the Seldinger technique. The length of the sheath may be in the range of from 5 cm to 15 cm, or from 10 cm to 12 cm. The inner diameter may be in the range of from 7 Fr (1 Fr=0.33 mm) to 10 Fr, or 8 Fr.

The illustrated embodiment shows reverse flow through the catheter. Alternatively, reverse blood flow may pass through the sheath. In another embodiment, reverse flow can occur through either the sheath or the catheter, and procedure devices can pass through whichever of the sheath or catheter that is not being used for reverse flow.

This configuration provides many advantages and alternatives. Reverse flow can pass through the conduit, the sheath, or both. The conduit may be connected to a shunt, receptacle bag, or vein (e.g., IJV or femoral vein). The catheter comprising conduit 112 may be used without impinging the function of the sheath, and vice-versa. As noted above, a vascular surgeon is not required. Also this access device configuration is suitable for use with a cervical (carotid) or femoral access. In another embodiment, access is cervical, primarily because such a location saves approximately ten minutes procedure time over femoral access, thus reducing the patient time in surgery and decreasing the amount of time the patient is subject to stroke risk.

The arterial access device can have various features particularly useful in a retrograde blood flow system. As shown in FIG. 1, the arterial access device 110 can include a flow lines 615 and 915 and a Y-adaptor to connect the sheath to a retrograde flow system. Optionally, the distal sheath may include an occlusion element 129 for occluding flow through, for example the CCA. If the occluding element 129 is an inflatable structure such as a balloon or the like, the sheath can include an inflation lumen that communicates with the occlusion element 129. The occlusion element 129 can be an inflatable balloon, but it can also be an inflatable cuff, a conical, or other circumferential element which flares outwardly to engage the interior wall of the carotid artery to block flow, a membrane-covered braid, a slotted tube that radially enlarges when axially compressed, or similar structure which can be deployed by mechanical means, or the like. In the case of balloon occlusion, the balloon can be compliant, non-compliant, and elastomeric; reinforced; or have a variety of other characteristics. In an embodiment, the balloon is an elastomeric balloon which is closely received over the exterior of the distal end of the sheath prior to inflation. When inflated, the elastomeric balloon can expand and conform to the inner wall of the carotid artery. In an example of the present disclosure, the elastomeric balloon is able to expand to a diameter at least twice that of the non-deployed configuration, frequently being able to be deployed to a diameter at least three times that of the un-deployed configuration, at least four times that of the un-deployed configuration, or larger.

In some embodiments of the present disclosure, the arterial access device may include a catheter having a backstop; a balloon, typically attached to a central guidewire; and a knot or the like (some other geometrically shaped element) extending on the guidewire outwardly and distally from the balloon. In use, the knot may be deployed in the region of the plaque or obstruction, and the knot may be used to loosen particles in the artery, which flow back toward the backstop and/or the catheter. The balloon may then be partially deployed, whereby particles may become trapped between the balloon and the end of the catheter (or backstop). The balloon may then be drawn back into the catheter, thereby drawing and capturing particles within the lumen of the catheter. The catheter, carrying the particles, may then be pulled out of the body.

Alternative elements or structures of the system described in the present disclosure may include a guidewire with a distal tip comprising a kite tail shaped element; a backstop comprising a funnel shaped cage; and a balloon that is deployed and/or expanded in stages, e.g., the proximal end first, thereby forcing, pushing, or capturing particles into the backstop.

The system 100 is adapted to regulate retrograde flow in a variety of manners. Any combination of the pump, valve, syringe, and/or variable resistance component can be manually controlled by the user or automatically controlled via a controller to adjust the retrograde flow rate. Thus, the system 100 can regulate retrograde flow in various manners, including controlling an active flow component (e.g., pump, syringe, etc.), reducing the flow restriction, switching to an aspiration source (such as a pre-set Vaculok syringe, Vacutainer, suction system, or the like), or any combination thereof.

Methods of Use

In an exemplary method of the present disclosure, the distal sheath of the arterial access device 110 is introduced into a carotid artery and into the ICA. As noted above, entry into the carotid artery can be via a transcervical or transfemoral approach, or any approach suitable for introducing a distal portion of a catheter into the OA. After the sheath of the arterial access device 110 has been introduced into the ICA, the blood flow will continue in an antegrade direction with flow from the OA entering both the ICA and the ECA.

The venous return device 115 can then be inserted into a venous return site, such as the IJV. The shunt 120 can be used to connect the flow lines 615 and 915 of the arterial access device 110 and the venous return device 115, respectively (as shown in FIG. 1). In this manner, the shunt 120 provides a passageway for retrograde flow from the atrial access device 110 to the venous return device 115. In another embodiment, the shunt 120 can connect to an external receptacle rather than to the venous return device 115.

Once all components of the system are in place and connected, flow through a carotid artery, ICA, or OA can be stopped, such as by using the occlusion element 129 as shown in FIG. 1. The occlusion element 129 can be expanded at a location proximal to the distal opening of the sheath to occlude the OA. Alternately, the tourniquet 2105 or other external vessel occlusion device can be used to occlude the OA to stop flow. In an alternative embodiment, the occlusion element 129 can be introduced on second occlusion device 112 separate from the distal sheath 605 of the arterial access device 110. The OA can also be occluded with a separate occlusion element, either on the same device 110 or on a separate occlusion device.

At that point, retrograde flow from the OA and ICA can begin and can flow through the sheath, the flow line 615, the shunt 120, and into the venous return device 115 via the flow line 915. The flow control assembly 125 can regulate the retrograde flow as described above. While the retrograde flow is maintained, a stent delivery catheter can be introduced into the sheath. The delivery catheter can be introduced into the sheath through a hemostasis valve and the proximal extension of the arterial access device 110. The delivery catheter can be advanced into the ICA and the OA.

Vibrating Guidewire

Some embodiments of the present disclosure may include a conventional guidewire. For example, a guidewire with a basket or the like on the distal end, or a guidewire having a geometrically shaped element on the distal end.

This guidewire is intended for neuro interventional procedures in which a reverse flow system is in use. The guidewire is designed to be used in cervical access where there is a need to remove plaque from a specific arterial segment. Once reverse flow is established, the guidewire is placed in the location of the stenosis and a vibration is induced via an electric motor. This vibration may loosen material either due to direct contact with general vibration, or with contact and by use of a specific resonance frequency of the target material for removal. The guidewire is of general design, however it is optimized for cervical access procedures and is designed to fit within the vibratory motor housing in such a way as to contact the motor. Contact with this motor imparts a vibration in the guidewire which is transmitted to the target anatomy and serves to aid in the removal of plaque.

In some embodiments, the vibratory motor is positioned on and or attached to a surgical drape. It is intended that the vibratory motor should remain substantially stationary. The guidewire passes through or is attached to the vibratory motor. Positioning in the target anatomy is accomplished by moving the guidewire in and out of the arterial segment being treated.

Vibrating Angioplasty Balloon

The present disclosure includes a balloon, which may be a conventional balloon or may include geometric features intended to facilitate plaque/obstruction removal or dislodgement. Balloons may be of any of a variety of shapes (asymmetrical, spiral, etc.) and/or coated with materials for facilitating plaque removal (abrasives, etc.).

This balloon is intended for neuro interventional procedures in which a reverse flow system is in use. The balloon is designed to be used in cervical access where there is a need to remove plaque from a specific arterial segment. Once reverse flow is established, the balloon is placed in the location of the stenosis and a vibration is induced via an electric motor. This vibration may loosen material either due to direct contact with general vibration, or with contact and by use of a specific resonance frequency of the target material for removal. The balloon is of general design, however it is optimized for cervical access procedures and is designed to fit within the vibratory motor housing in such a way as to contact the motor. Contact with this motor imparts a vibration in the balloon which is transmitted to the target anatomy and serves to aid in the removal of plaque.

In accordance with the present disclosure, the vibratory balloon, and/or the vibratory guidewire may loosen plaque or an obstruction, and plaque/obstruction particles and the like may be removed from the site using the reverse flow system.

In another embodiment, a medical device or agent is capable of delivering drugs to the ostium for the purpose of improving vascular blood flow at the ostium and within the OA. Exemplary drugs include, but are not limited to, low dose Viagra (or equivalent PDE 5 inhibitor), Lucentis, Avastin, Taxol, Rapamyacin, or other pharmaceuticals used to improve vascular blood flow.

Figure 3A:
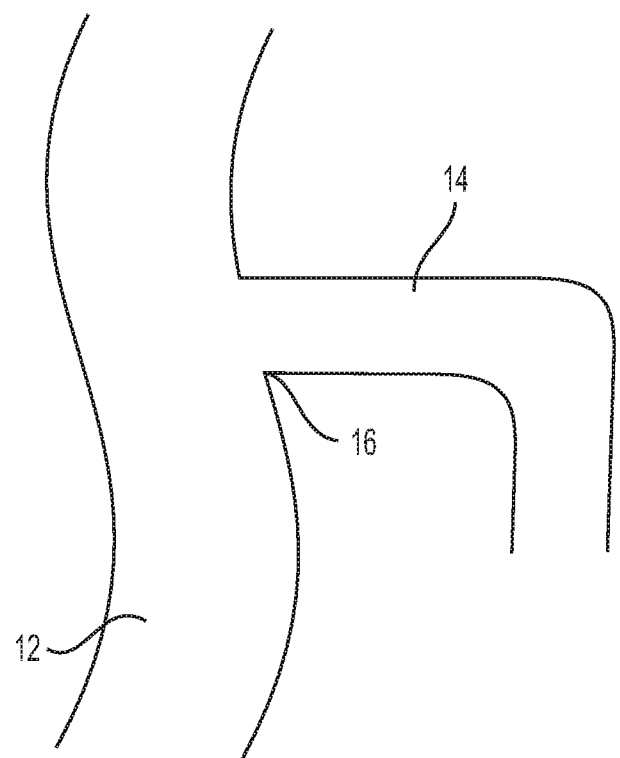
FIGS. 3A and 3B illustrate exemplary vasculature of the eye of a subject.
Figure 3B:
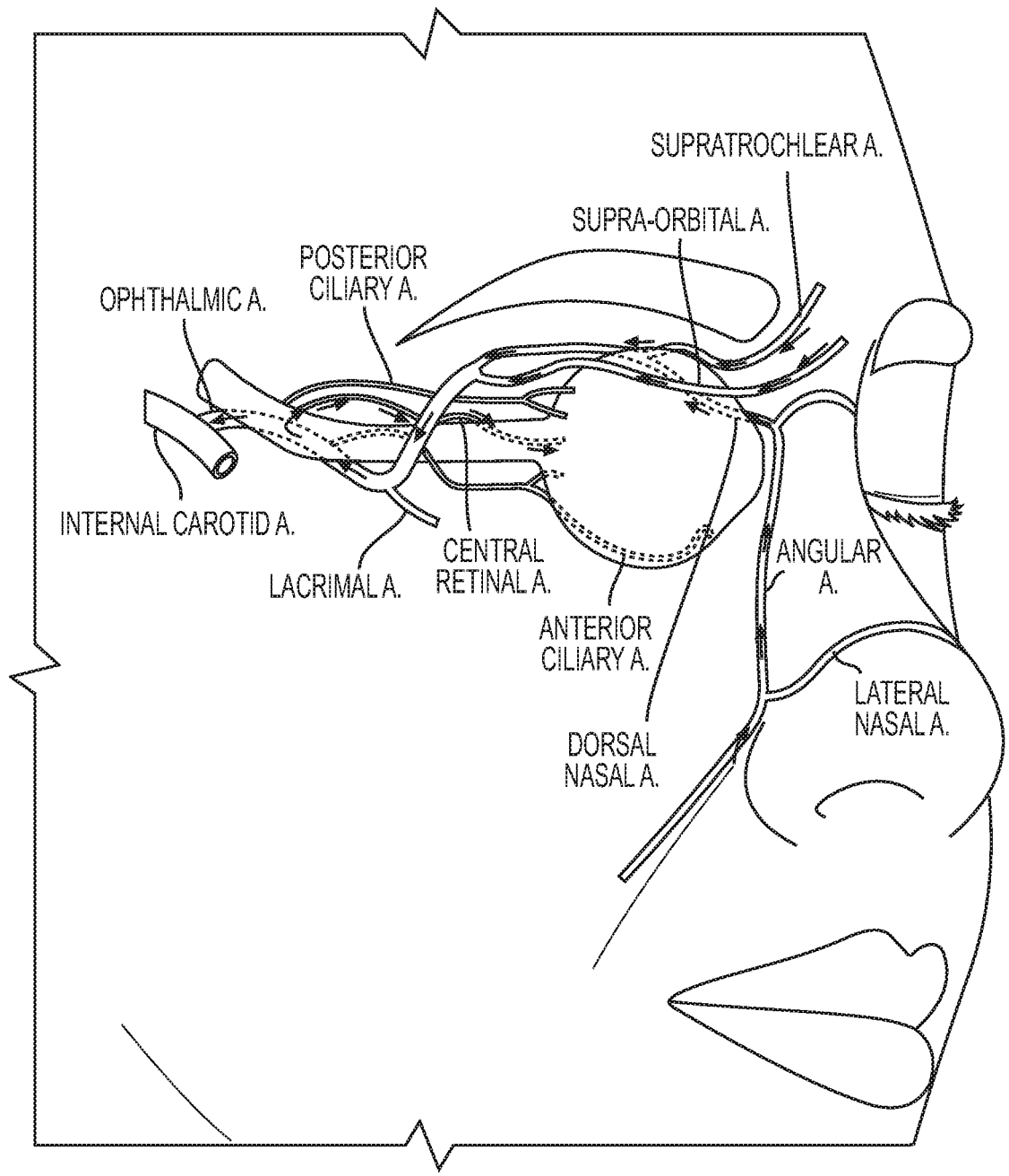
Figure 5:
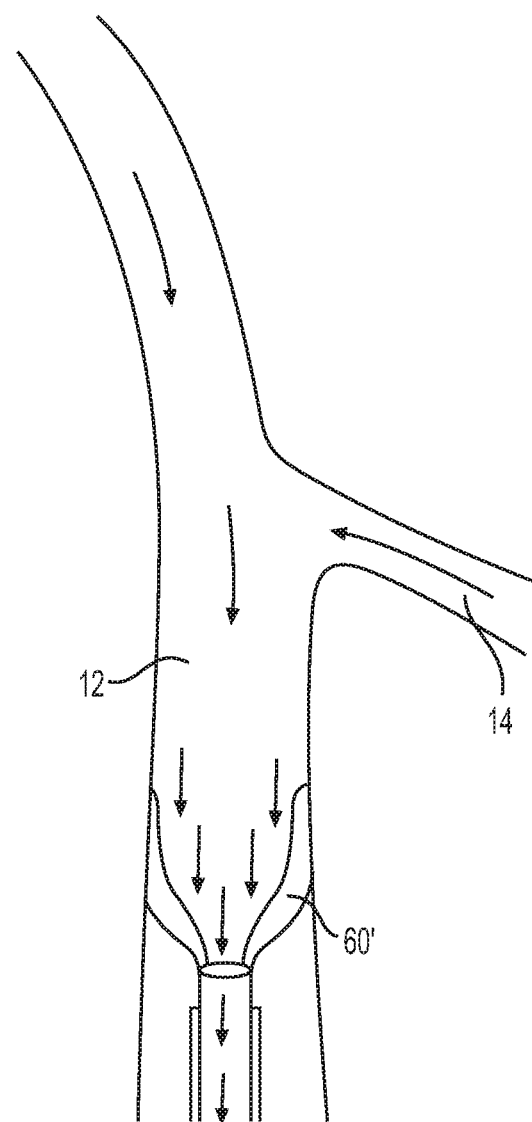
FIG. 5 illustrates an exemplary sheath and flow direction balloon within an ICA, according to an aspect of the present disclosure.
Figure 6:
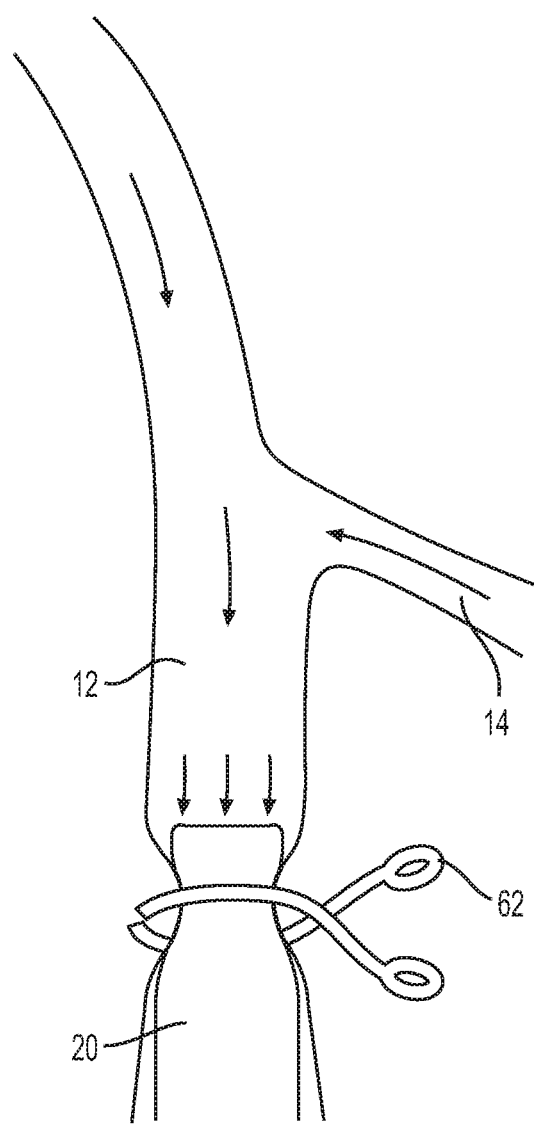
FIG. 6 illustrates an exemplary sheath within an ICA, and a flow direction element about the artery, according to an aspect of the present disclosure.

FIGS. 3A and 3B illustrate exemplary anatomy relating to an eye of a patient or subject. The vasculature in the fluid flow path to and from the eye, the rear of the eye, portions of the eye, or regions near the eye, includes, among other arteries and veins, the ICA 12, the OA 14, and the junction 16 between the ICA 12 and the OA 14, which is also referred to as the ostium, as shown in FIG. 3A. In most patients, OA 14 extends at an acute angle relative to ICA 12, as shown in FIGS. 5 and 6. In some patients, a flap of tissue (not shown) may extend between OA 14 and ICA 12. That is, in some arrangements, the flap of tissue may be positioned in junction 16. Additional areas of the anatomy, as shown in FIG. 3B, may include the vascular system which is commonly referred to as the terminal branches. These areas include, but are not limited to, the SOA, the STA, the DNA, and the FA.

Diseases and conditions of the eye (e.g., AMD, glaucoma, diabetic retinopathy etc.) may result in decreased blood flow to and around the eye, which is believed to contribute to nutrient (e.g., oxygen) depletion in and around the eye. Without being bound by theory, it is believed that conditions that lead to lowered oxygen (or other nutrient) delivery to the tissue in and around the eye mediates and/or causes any of a variety of eye diseases, include, but are not limited to, AMD. Possible conditions include, but are not limited to, one or more of the following: blockage(s) in ICA 12; blockage(s) in OA 14; reduced blood flow anywhere in the fluid flow path between ICA 12 and eye tissue; reduced blood flow rate anywhere in the fluid flow path between ICA 12 and eye tissue; decreased hemoglobin amount or delivery to one or more eye tissues; and blockage(s) or reduced flow in any of the junctions or ostia between any of the vasculature between the ICA 12 and one or more eye tissues (e.g., junction 16).

According to aspects of the present disclosure, diseases and conditions of the eye may be directly mediated by improved blood flow to the vasculature of the eye (e.g., the posterior of the eye). For example, the systems, devices, and methods described herein may restore or increase the amount of oxygen (or other nutrient) that reaches the eye or an eye area which may include removing or opening a blockage (or partial blockage) in one or more vascular systems that support the eye. Opening a blockage or partial blockage may include increasing or restoring blood flow to or around the eye. Increasing blood flow may include, but is not limited to, increasing the blood flow rate. That is, aspects of the present disclosure may be directed to one or more intravascular medical devices and/or methods intended or configured to sufficiently unblock or at least partially restore blood flow in a blocked or partially blocked artery such that nutrient (e.g., oxygen) content is increased distal to the blockage. For example, in some aspects, the present disclosure is directed to devices and methods for restoring blood flow through the ostium or junction 16.

In additional aspects, the disclosure is directed to using such devices and methods to restore or increase blood flow and/or or restore or increase nutrient (e.g., oxygen) levels, to the eye or a portion thereof. Restoring or increasing oxygen flow may include using the devices and methods described herein, or equivalent devices and methods, but is not to be limited thereby. Various conditions or diseases of the eye may be treated according to embodiments of the disclosure. Exemplary conditions and diseases are described in U.S. Provisional Patent Application No. 62/396,091, entitled "Systems and Methods for Treating Eye Diseases Using Retrograde Blood Flow," filed Sep. 16, 2016, and incorporated by reference herein in its entirety.

Exemplary embodiments of the present disclosure provide a reverse flow or retrograde flow device and system for the treatment of an eye, including the treatment of any diseases or conditions of the eye. Such a reverse or retrograde flow may protect the brain or the eye from the possibility of an embolic event or other damage during a cerebral interventional procedure.

In exemplary embodiments of the present disclosure, the resistance of blood flow through the system from the arterial side to the venous side may be reduced by a cervical approach. In some arrangements, one or more devices or sheaths may be inserted through the skin of a face of a subject. In certain embodiments of reverse flow systems, as will be described below, tubing, stopcocks, hemostasis valves, and blood/particulate filters with large lumens and/or high flow throughput may be used. In some embodiments, the device may be about 8.5 French (2.83 mm) to about 9.0 French (3 mm). In addition, the length of the tubing may be minimized, which when combined with larger luminal diameters and high flow blood/particulate filters, may result in reducing resistance to blood flow through the system from the arterial side to the venous side. Certain embodiments, as also described below, include a dedicated circuit to provide for reverse blood flow in the OA during the reverse flow procedure.

As will be discussed below in connection with the figures, a reverse flow system according to an exemplary embodiment may include some or all of the following components: two percutaneous sheaths (including a first arterial sheath and a second venous sheath); intravenous tubing with a low flow resistance blood/particulate filter and connecting the sheaths between the arterial and venous sheath access points; two stopcocks, a first stopcock containing a hemostasis valve on the arterial side of the blood filter near the arterial sheath; and a third sheath inserted into one of the terminal branches of the OA, and connected via a hemostasis valve to the intravenous tubing. The tubing is connected to a port of the stopcock attached to the arterial sheath. This exemplary arrangement represents a separate circuit which takes blood from the arterial sheath and feeds it into a terminal branch of the OA thereby inducing reverse flow in the OA. Additional components may include, on the venous side of the blood filter, a single stopcock. The stopcocks may be designed to maximize the luminal diameter such that resistance to blood flow from the arterial side to venous side of the system is minimized. Minimizing the blood flow resistance of the system will maximize the speed and ability of the system to remove potential embolic material from the artery under reverse flow and return arterial blood to the venous system.

Figure 4:
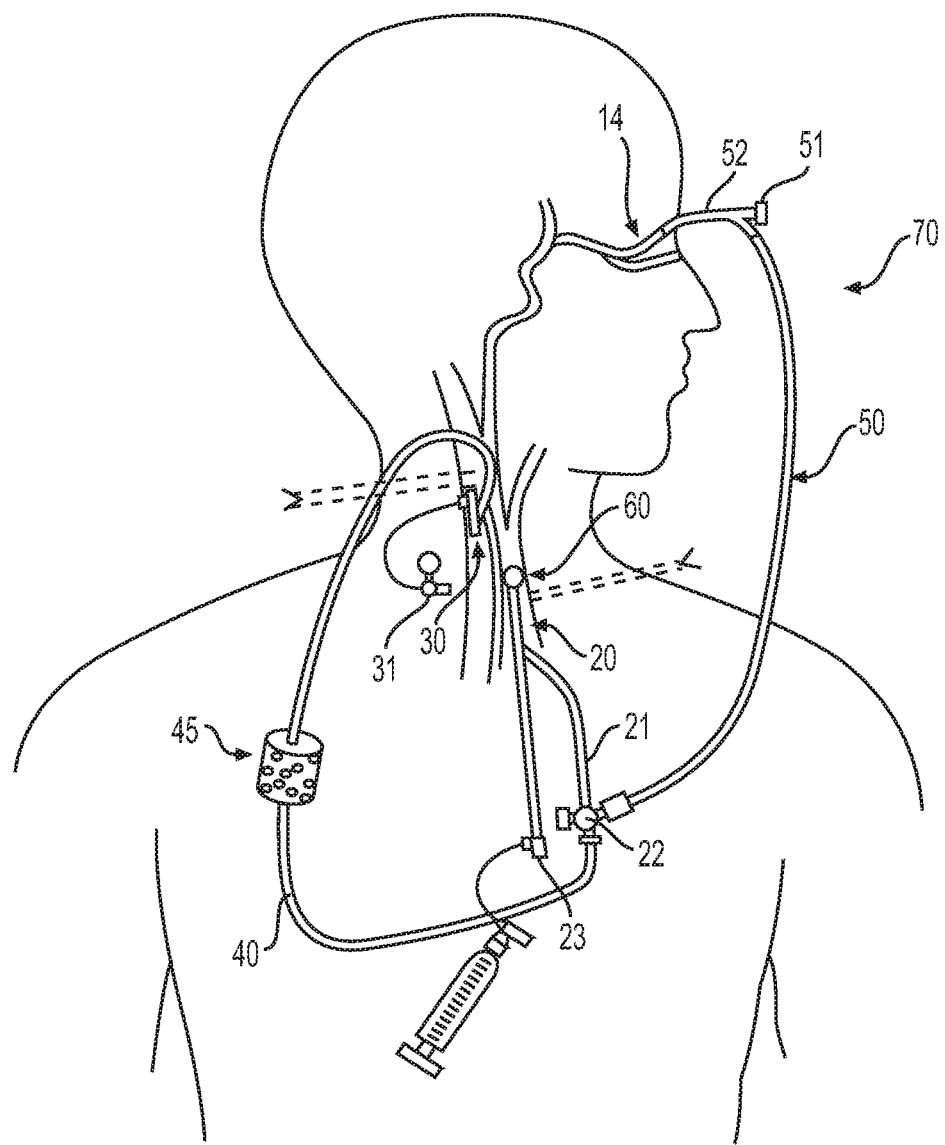
FIG. 4 illustrates an exemplary reverse flow system according to an aspect of the present disclosure.

In one exemplary embodiment shown in FIG. 4, a flow reversal system 70 includes: (i) an arterial sheath 20 having proximal and distal ends with a lumen extending therethrough; (ii) a venous sheath 30 having proximal and distal ends with a lumen extending therethrough; (iii) an expandable occluder 60 at the distal end of arterial sheath 20; (iv) a venous return circuit 21 at or near a distal end of sheath 20 proximal to expandable occluder 60; (v) a conduit 40, with a particulate/blood filter 45 interspersed, fluidly connecting a proximal opening of arterial sheath 20 to the venous sheath 30; and (vi) a circuit 50 connecting an arterial sheath stopcock 22 with a terminal branch of OA 14 (while the STA is depicted in FIG. 4, any other terminal branch/vessel downstream from OA 14 may be used) via a sheath 52. Arterial sheath 20 is placed in the CCA, though it could be placed in ICA 12, and the venous sheath is placed in the IJV, though other venous vessels may be used. A pressure gradient is created so that blood flows into the distal opening of arterial sheath 20, through conduit 40, and exits through a return port into the venous sheath 30. Flow reversal system 70 may be cervically-placed. Additionally, as shown in FIG. 4, arterial sheath 22 may further include an additional stopcock 23, venous sheath 30 may include a venous stopcock 31, and sheath 52 may include a stopcock 51.

An additional connection to the arterial sheath 20 includes circuit 50 that connects to sheath 52 placed in a terminal artery of OA 14 such that a portion of blood flow from the arterial sheath 20 is sent through circuit 50 and into the terminal artery of OA 14 for the purpose of reversing flow in OA 14, other arteries, and/or other arteries that supply blood to the eye.

Without intending to be bound by theory, it is believed that blocking the flow of blood facilitates the reversal of blood flow across a treatment site. In an example of the present disclosure, expanding expandable occluder 60 in the CCA blocks the flow through the CCA and causes the pressure on the downstream side, e.g., distal side of expandable occluder 60, to drop, thereby facilitating blood from contralateral vessels to flow toward the lower pressure and flow into arterial sheath 20, which carries embolic debris into the blood/particulate filter 45.

In embodiments of the present disclosure, the expandable occluder 60 can be any shape which occludes a radial space about the distal region or end of the arterial sheath 20, so as to ensure blood and emboli is directed into the distal opening of the arterial sheath 20, rather than becoming trapped between an intraluminal wall of the blood vessel and an outer wall of arterial sheath 20. For example, expandable occluder 60 can be disc-shaped, donut-shaped, cylindrical, cone-shaped, funnel-shaped, or any other shape that substantially occludes the flow of blood about the radial space of the distal region of the arterial sheath 20 and defines the outer wall of the arterial sheath 20 to permit blood to pass through the distal opening of the arterial sheath 20. FIG. 5 shows an exemplary cross section of the placement and structure of a flow direction balloon 60' in the ICA 12, which is an alternative to placement in the CCA. As shown, flow direction balloon 60' may include a tapered cylinder or cone shaped balloon having a proximal end coupled to a distal end of arterial sheath 20 and may guide or otherwise facilitate a flow of blood through arterial sheath 20. That is, a wall or surface of balloon 60' may narrow towards a distal end of arterial sheath 20, and contact a wall of ICA 12 at distal portions of balloon 60'.

Embodiments of the present disclosure also include a retrograde flow system that does not require the use of a balloon or the like. In these systems, methods, and assemblies, the flow direction element applies an external force applied to an artery to compress the artery around the sheath 20. Such an embodiment is shown in FIG. 6, where the external force is provided by a clamp 62.

Embodiments of the present disclosure include any tool or device that functions to apply force, to clamp, or to close the artery against sheath 20. Exemplary elements include, but are not limited to, a clamp, a vise, a band, a suture, a pincer, a contractor, a constrictor, and the like. Any such element compresses or closes the artery against the sheath 20, thereby forcing any blood flow through the lumen of the sheath 20 rather than around the sheath 20.

In other embodiments of the present disclosure, the flow direction element of the system is used to initiate the reversal of flow in the CCA (or the ICA 12). For example, flow reversal may be accomplished by use of an expandable occluder 60, such as an inflatable balloon device, e.g., balloon 60'. In another example, flow reversal may also be accomplished without a balloon by using a sheath that has external force applied to compress the CCA/ICA 12 against the tube portion of the arterial sheath 20. This compressive action serves to prevent blood flow around the arterial sheath 20 (in the same way as an inflatable balloon does from inside the CCA/ICA 12) and force blood through the arterial sheath 20 and into the venous circuit of the system, thereby providing flow reversal. The sheath may be of conventional design, or may contain elements that facilitate compressing the CCA/ICA against the arterial sheath 20 for the purpose of establishing flow reversal. These elements may include the following: (1) specific arterial sheath 20 durometer material design to accommodate compressive force while maintaining arterial sheath 20 lumen integrity; (2) radiopacity elements incorporated into the arterial sheath 20 to allow for confirmation of proper clamping position via fluoroscopy; and/or (3) incorporation of a distal sheath inflatable element (e.g., expandable occluder 60 and/or balloon 60') to aid in the direction of blood flow into the arterial sheath 20 lumen and to prevent blood leakage between the arterial sheath 20 and the CCA/ICA 12 during clamping.

In another embodiment of the present disclosure, the arterial access device may include a catheter or sheath 20 having a backstop (e.g., balloon 60'); and a central guidewire (not shown) for passing through a lumen of the sheath 20. The guidewire includes an attached inflatable balloon, and a knot, brush, or other geometrically shaped artherectomy-like element extending outwardly on the guidewire, distally of the balloon. In use, the element may be deployed in the region of a plaque or obstruction to loosen particles in the artery, which flow back toward sheath 20. The guidewire balloon may then be partially inflated/deployed, whereby particles may become trapped between the balloon and the end of the sheath 20 and balloon 60'. The guidewire balloon then may be drawn back into the sheath 20, thereby drawing and capturing particles within the lumen of the sheath 20. The sheath 20, carrying the particles, then may be pulled out of the body and/or the particles may be aspirated out of sheath 20.

Other embodiments of the present disclosure may include a guidewire with a distal tip comprising a kite tail shaped element; a backstop comprising a funnel shaped cage; and/or a balloon that is deployed and/or expanded in stages, e.g., the proximal end first, thereby forcing, pushing, or capturing particles into the backstop. Additional interventional procedures and devices are described below and in U.S. Provisional Patent Application No. 62/396,091, entitled "Systems and Methods for Treating Eye Diseases Using Retrograde Blood Flow," filed Sep. 16, 2016, and International Application PCT/US2017/021673, entitled "Systems and Methods for Treating Eye Diseases Using Retrograde Blood Flow," filed Mar. 9, 2017, both of which are incorporated by reference herein in their entireties.

As mentioned above, a purpose of reverse flow is to channel embolic debris of a wide range of particle sizes away from particularly at-risk areas during an endovascular treatment. In an embodiment of the present disclosure, blood, along with embolic debris in some embodiments, from the treatment site is rerouted through a sheath/catheter to another location, for example from high to low pressure. A filter (e.g., filter 45) can be included to capture embolic debris from the blood. Once the blood passes through the filter, the blood may be re-introduced into the venous circulation.

Some embodiments of the present disclosure include methods of achieving reverse flow in cerebral vasculature, and, for example, in the OA 14 and ICA 12. In some examples, prior to performing the method, a duplex ultrasonography scan may be performed to measure the distance between the planned puncture site and the carotid bifurcation and also to confirm the anatomical status of the CCA.

To reverse blood flow, according to an embodiment of the present disclosure, the following steps may be taken:

1) A small 4 cm transverse incision is made at the base of the neck between the two heads of the sternocleidomastoid muscle. The CCA is dissected free for about two centimeters, as well as the IJV. A vessel loop is placed around either vessel.

2) A 9 French venous sheath, e.g., sheath 30, is inserted in the caudal direction over a wire after puncturing the jugular vein.

3) An arterial sheath 20 is inserted in the CCA in a cephalad direction using a guidewire. The arterial sheath 20 has a stopcock 22 attached to the proximal end of the arterial sheath 20. The guidewire may be a stiff 0.035" guidewire introduced in the ECA under fluoroscopic.

4) An additional, appropriately sized arterial sheath (e.g., sheath 52) is inserted into a terminal artery of OA 14 and connected via intravenous tubing (e.g., circuit 50) to the arterial sheath stopcock 22.

5) The three-way-stopcock 22 is opened to allow the blood to fill the tubing or conduit 40 and the filter 45. The stopcock of the arterial line is opened and then, after flushing blood, is connected to the venous tubing establishing the fistula.

6) The occluding element (e.g., balloon 60') on the distal tip of the large lumen arterial sheath 20 is inflated in the CCA. At this moment, flow reversal is established, and the OA 14 sheath 52 stopcock 51 is opened to establish reverse flow in the OA 14 circuit. A small injection of contrast media through the side-port of the arterial sheath will confirm that flow is reversed.

According to this method, a temporary, reversible arteriovenous fistula can be created between the CCA (or the ICA 12) and the jugular vein at the base of the neck through, for example, a small incision done under local anesthesia. The fistula produces a temporary reversal of flow of the ICA 12 or the OA 14, which may itself unblock the OA 14, or while an interventional procedure may be performed. This flow reversal allows particulate to be removed from the bloodstream during an intervention procedure, to not pose a cerebral or eye embolic threat or damage.

After creating the fistula, the operator may commence an interventional procedure. The interventional procedure may include providing one or more stents implanted in the vasculature supplying blood to the eye. For example, a stent may be placed in ICA 12, OA 14, or at the ostium or junction 16 of ICA 12/OA 14. The stent may provide patency. The stent may include radiopaque features to guide in accurate placement. Other interventional procedures may include use of a balloon in an angioplasty-like procedure, or performing an atherectomy. These procedures may restore and/or increase the amount of oxygen (or other such nutrients) being delivered to the eye. Devices, methods, therapies, or combinations that change the oxygen (or other nutrient) content in or near the eye include, but are not limited to, increasing the blood flow anywhere in the vasculature leading to the eye or a portion of the eye; removing or opening an obstruction in the fluid flow path in the vasculature leading to the eye; delivering and deploying a stent in the fluid flow path in the vasculature leading to the eye; using atherectomy or similar devices to physically remove portions of any obstructions in the vasculature leading to the eye or portion of the eye; and localized drug and/or an oxygen device for increasing flow or amount of oxygen in one or more eye tissues. In some embodiments, a device or method of the present disclosure may be combined with a known or new drug or oxygen device in order to treat one or more eye diseases or conditions. The present disclosure provides for an apparatus for deployment of a detachable diagnostic or therapeutic implant device such as a stent, embolic coil, or other vascular occlusion device using a catheter, whereby placement of a stent or the like in a portion of the carotid artery changes the diameter of the ICA 12 and/or OA 14, which in turn increases blood flow between the ICA 12 and the eye.

Exemplary interventional procedures, and implants, catheters, guidewires, balloons, and other therapeutic devices for use in interventional procedures, according to embodiments of this disclosure, are described in the following documents, U.S. Provisional Patent Application No. 62/396,091, entitled "Systems and Methods for Treating Eye Diseases Using Retrograde Blood Flow," filed Sep. 16, 2016; and U.S. patent application Ser. No. 15/609,547, entitled "Devices and Methods for Treating Occlusion of the Ophthalmic Artery, filed May 31, 2017, both of which are incorporated by reference herein in their entireties.

It is intended that this disclosure should not be limited by the type of procedure (cervical) or use of specific instruments necessary to provide an interventional result. For example, in accordance with this disclosure, eye disease may be treated using at least one arterial access device, using a percutaneous transfemoral approach; a transcervical approach; cervical access; or combinations thereof. Exemplary access procedures and devices are described in U.S. Provisional Patent Application No. 62/396,091, entitled "Systems and Methods for Treating Eye Diseases Using Retrograde Blood Flow," filed Sep. 16, 2016, and incorporated by reference herein in its entirety.

In accordance with this disclosure, a reverse flow system may be established in any location suitable for treating an eye disease or condition. These locations include, but are not limited to, the ICA 12, the ECA, the CCA, the SOA, the STA, the OA 14, and an appropriate site in the venous system, including, but not limited to, the IJV or the femoral vein.

The present disclosure also relates to medical devices and therapies for treating occlusion of the OA, and specifically, to novel interventional devices for restoring and/or increasing vascular blood flow to the rear of the eye.

Without intending to be bound by theory, it is believed that the primary causative effect for WAMD, glaucoma and diabetic retinopathy is occlusion of the OA such that normal blood flow is restricted (ischemia) to the rear of the eye. As a result of this ischemia, hypoxia (resulting in neovascularization) is induced in these structures and vision eventually devolves into a dysfunctional retina (WAMD). From this, the present disclosure describes possible devices that may be used to provide a treatment methodology for WAMD, which may include a device(s) for performing interventional work in the OA and surrounding structures to restore/increase vascular blood flow, and a device for selectively inducing retrograde blood flow in the retinal vasculature via manipulation for IOP.

The present disclose includes an interventional device designed to gain access to and deliver direct mechanical and/or drug therapy to a specific location of the anatomy. While the following examples specifically detail the necessary components for a particular OA application, this technology may be used in any anatomical location in which removal of material is desired in a luminal environment. This environment may be vascular or not and may be used in any tubal, luminal or other similar anatomical structure where removal of material is desired. As such, some embodiments may be scaled, modified or constructed such that it can provide therapy for a specific luminal anatomical location/need. In some embodiments, the interventional device design may be based on a central wire, hypotube, coil, balloon or combination thereof. In other embodiments, the interventional device may be made of stainless, nitinol, polymer, other materials, or a combination thereof, and designed to accommodate specific approaches (carotid, subclavian, femoral, endoscopic or laparoscopic). For example, entrance into the body may be provided by a vascular access element which may be typical, or may be designed specifically for use with a device according to the present disclosure (e.g., catheter sheath introducer or equivalent). The disclosed device fits within a sheath, which is designed to provide a protective element for the device as well as to prevent vessel trauma during delivery to the target site. The distal portion includes the ability to provide distal protection in the OA, as well as an element to provide diametric interference. This area of diametric interference is designed to interface with the target vessel segment (e.g., lesion) such that specific and deliberate manipulation provides for the ability to selectively remove material from the lesion site. The diametric interference element also provides for the ability to compress such that it fits within the device sheath to provide a minimal diametric dimension. This diametric portion is also referred to as an interventional element. Once the device is placed at the target anatomy, the interventional element is positioned such that it is outside the sheath and it conformally fits the inner diameter of the target anatomy. The interventional element also contains a design element that allows for tissue removal when manipulated in a specific manner. That manner includes manual rotation, manual push/pull, mechanical rotation, mechanical push/pull, site specific drug delivery or a combination of some or all of those. Additionally, the tissue removal device and conforming element is optionally different devices, two devices or different segments of the same device. Once material removal is complete, the interventional element is pulled into the sheath, along with the distal protection portion (equipped) of the device and the entire assembly removed. It is also possible to remove the interventional element for cleaning and to replace and continue. Furthermore, this device may deliver drug therapy directly to the area of intervention. For example, delivery of a pharmaceutical compound to reduce the rate of restenosis may be possible as well as a variety of other pharmaceutical compounds. The device is also constructed such that it is able to provide interventional therapy in the form of energy delivery. This includes, but is not limited to, laser, ultrasound, cryogenic, radiofrequency (RF), and/or other energies or combination thereof. Additionally, there is also the provision for the ability to provide direct optical viewing of the target site prior to, during, and after administration of therapy. There is an ability to combine multiple drug therapies for a single condition or multiple conditions. For example, Sirolimus for antiproliferative effect post angioplasty. In addition to this or separate from this, a statin may be included and eluted as lipid-like deposits called drusen can be concomitant to WAMD. It is presumed that the slow elution of a statin would reduce the size and number of drusen deposits and thereby improve eyesight.

Interventional Device—Common device elements:
1. Ability to visualize under fluoroscopy
2. internal carotid access (can be done via subclavian or femoral)
3. Distal protection element in the ICA
4. Distal protection element in the OA
5. Works in OA diameter ranges between 0.7 mm to 1.4 mm—derived by atmospheric pressure applied to the conformal element
6. Working length for OA estimated to be about 15 inches, further definitions included
7. Approaches other than ICA also included
8. Ability to remove material from the OA and transport out of the vasculature
9. Ability to induce retrograde flow, either continuously, or on demand for specific time periods
10. May use a guiding catheter to cannulate the OA from the ICA (combination of GC features with sheath to have an 'all in one')

Figures 7A, 7B:
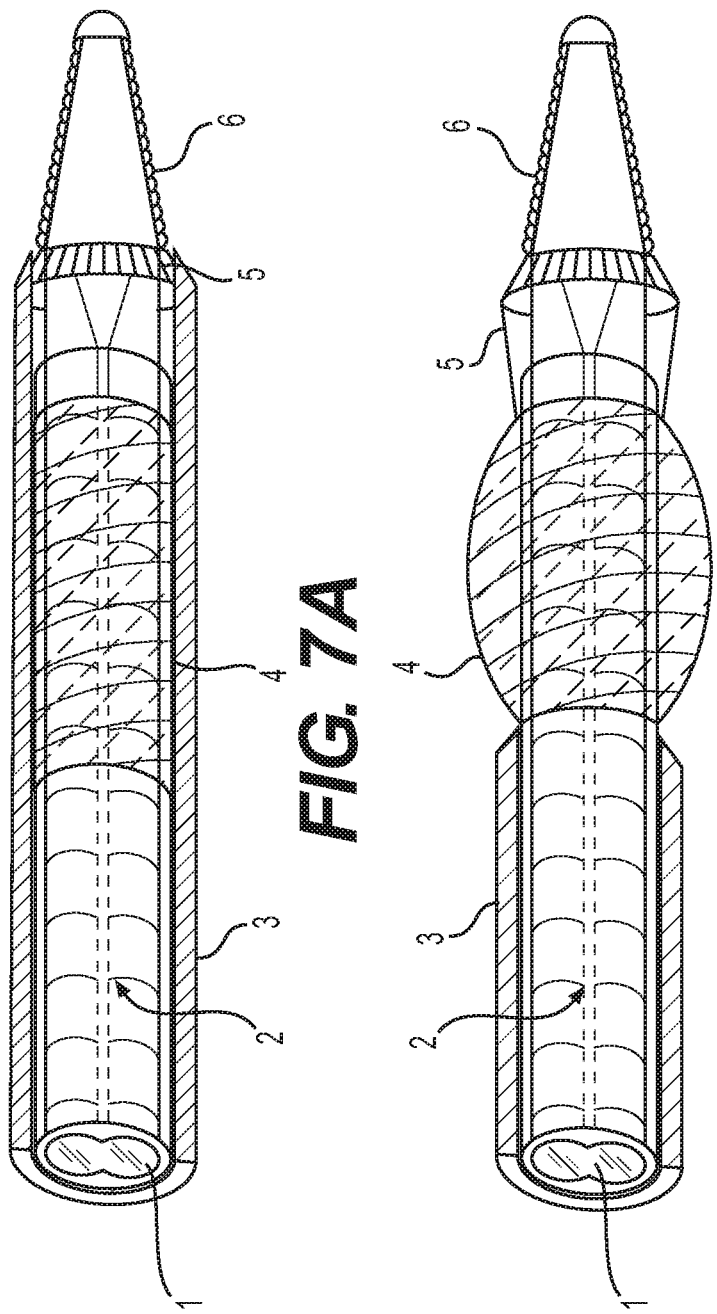
FIGS. 7A and 7B illustrate an exemplary semi-transparent perspective side view of an embodiment, according to an aspect of the present disclosure.

Interventional Device—Singular elements (specific to a particular design):
1. Distal OA protection as an integral element of the device
2. Distal OA protection as a separately placed/removed device
3. Distal CA protection as an integral element of the device
4. Distal CA protection as a separately placed/removed device
5. Distal ICA protection as a integral placed/removed device
6. Distal ICA protection as a separately placed/removed device
7. Ability to deliver an RF element for therapy
8. Ability to deliver a laser element for therapy
9. Ability to deliver an ultrasound element for therapy
10. Ability to deliver a cryogenic element for therapy
11. Ability to deliver drugs via infusion
12. Ability to deliver drugs via injection (e.g., bolus—tissue plasminogen activator (TPA))
13. Drug delivery capability before, during and after material removal
14. Ability to deliver drugs via micro needles IA. Interventional Device—Specific Examples: Solid corewire based FIGS. 7A and 7B show an embodiment of the present disclosure having an Aspiration Core. The design is based on a solid metallic corewire with integrated aspiration capability. The device consists of the following elements and features as detailed in FIGS. 7A and 7B:
1. Center corewire
2. Longitudinal indentations
3. Delivery sheath
4. Cutting element
5. Distal protection element
6. Atraumatic tip FIG. 7A depicts the device with the delivery sheath 3 covering the cutting 4 and distal protection 5 elements, which are both mounted on the central core 1. The tip of the device contains an atraumatic tip 6 to aid in placement of the device.

FIG. 7B depicts the delivery sheath pulled back and the cutting and distal protection elements both in a deployed position. Aspiration is accomplished by either flushing and aspirating using alternate longitudinal channels 2 of the corewire, or by a combination use of longitudinal channels and the delivery sheath, one for flushing and the other for aspiration. Once the procedure is complete, the device is withdrawn back into the delivery sheath and positioned as seen in FIG. 7A. The device is then safely withdrawn from the anatomy.

Generally, the overall length of the device is optimized for the anatomical location and approach. For example, for use within the OA, an overall length of about 160 cm or about 15.00 inches for the device would be used in conjunction with an appropriately designed sheath. The maximum overall diameter of the sheath would be about 1.0 mm range (after inflation), with the cutting and distal protection elements offering a conformal fit capability in the deployed range of between 0.7 mm to 1.4 mm as dictated by the specific dimensions of the OA and the lesion site. These overall length and diametric dimensions would be adjusted based on the specific applications and is contemplated as within the scope of the present disclosure. In addition, the specific material composition, formulation and manufacturing parameters of material used would be refined to address the specific application and is contemplated as within the scope of the present disclosure. This dimensional information applies to all of the designs disclosed. In one example, the lesion crossing profile of this device is less than 0.2 mm. A range of appropriate profile dimensions is contemplated as within the scope of the present disclosure.

A. Interventional Device—Specific Examples: Plain Core—Non Aspiration Core

Figure 8:
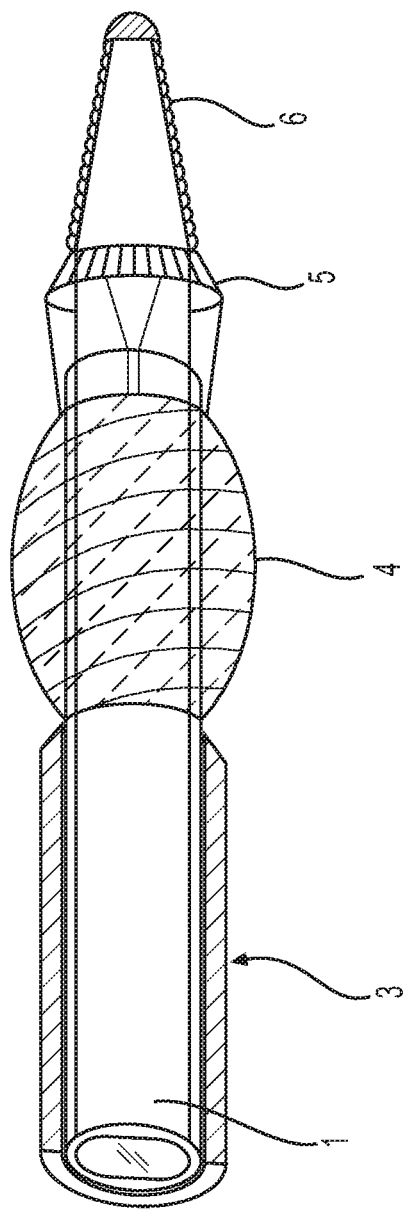
FIG. 8 is an exemplary semi-transparent perspective side view of another embodiment of the present disclosure.

The design in FIG. 8 is based on a solid corewire and does not have specific aspiration capability. The device consists of the following elements and features:
1. Center corewire
3. Delivery sheath
4. Cutting element
5. Distal protection element
6. Atraumatic tip This disclosed subject matter of FIG. 8 is essentially the same as the FIGS. 7A and 7B aspiration core with the exception that the core is not designed to facilitate aspiration. The remaining elements of the device are essentially similar to the aspiration core design. FIG. 8 depicts the delivery sheath pulled back and the cutting and distal protection elements both in a deployed position. Once the procedure is complete, the device is withdrawn back into the delivery sheath and positioned in a similar fashion as seen in the aspiration core FIG. 7A. The device is then safely withdrawn from the anatomy.

It should also be noted that the corewire based design may include elements that are much simpler in design than illustrated in the sketch above. These designs could include a wire with a specific drawn profile that is inserted into the anatomy such that movement of the wire would allow an interface between the profile of the corewire and the anatomy to facilitate lesion material removal. These particular designs could include 1) a straight 'as drawn' wire, 2) an as drawn wire with a twist or 3) a selective combination of the two.

Figure 9B:
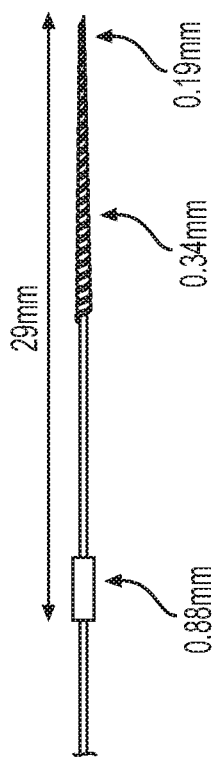
FIG. 9A illustrates an exemplary corewire and FIG. 9B illustrates an exemplary tapered corewire, according to an aspect of the present disclosure.
Figure 9A:
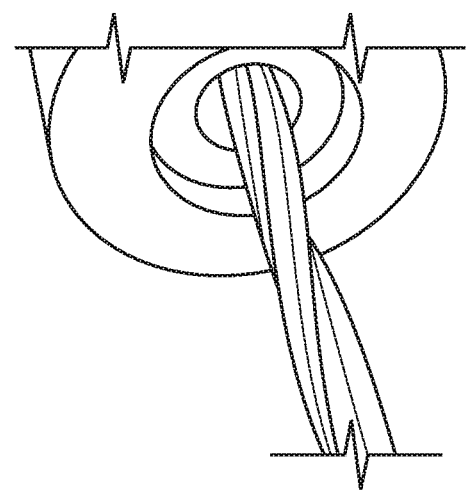

FIGS. 9A and 9B depict drawn wire with a twist and the distal tip segment of our initial corewire based prototype design.

Figure 10:
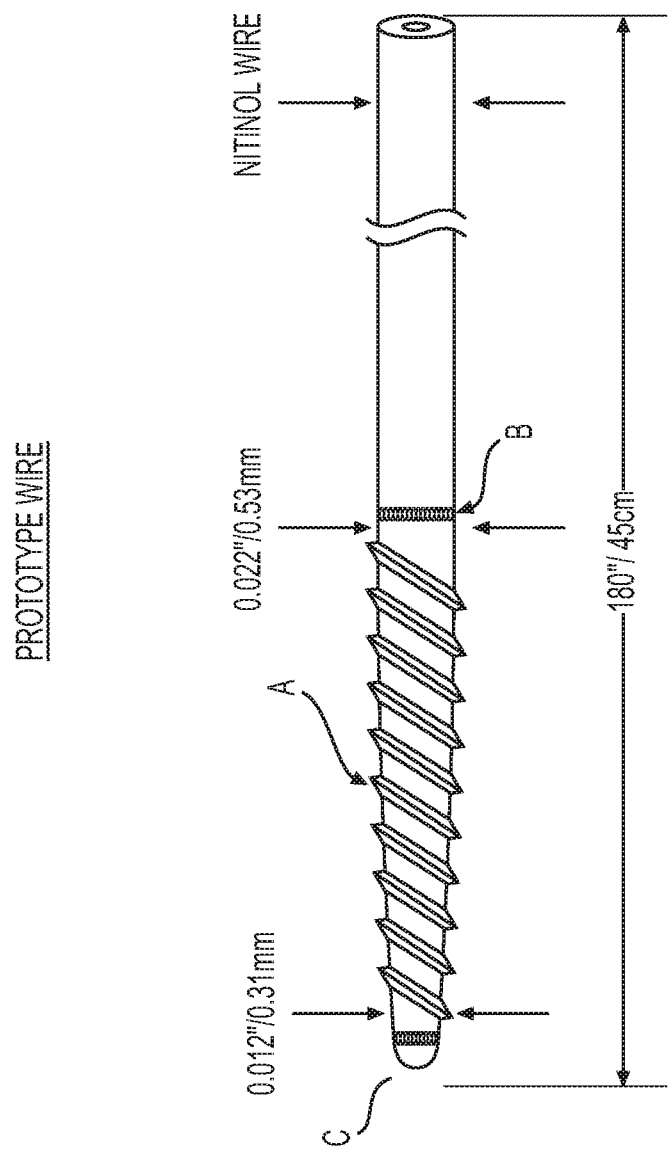
FIG. 10 illustrates an exemplary side view of an embodiment of the present disclosure.

FIG. 10 depicts the initial corewire based prototype overall configuration.

B. Interventional Device—Hypotube Based

Figure 11C:
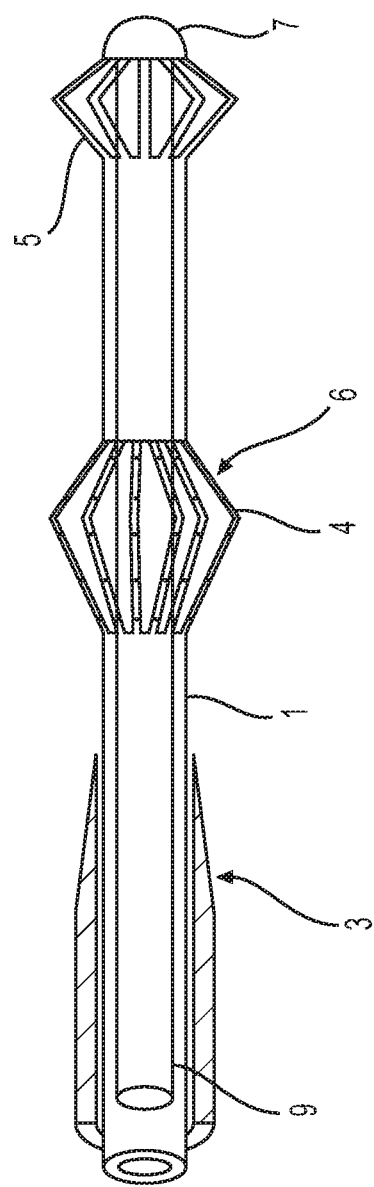
FIG. 11C illustrates an exemplary side view of an embodiment of the present disclosure.

Integral elements—The design in FIGS. 11A-11C is based on a hollow metallic tube. Aspiration capability is not detailed in this sketch, but may be possible with the addition of a central flush source. The device consists of the following elements and features as detailed in FIGS. 11A and 11B:
1. Central Corewire Hypotube
3. Delivery sheath
4. Cutting element
5. Distal protection element
6. Abrasives
9. Guidewire FIG. 11A depicts the device with the delivery sheath 3 covering the cutting 4 and distal protection 5 elements, which are both cut from the actual hypotube 1 and as such, are integral to the hypotube An alternative version of this design would be a hypotube version with cutting and distal protection elements mounted on the hypotube. There would also be a provision for an element that would be positioned in the lumen after removal of the guidewire. This element would serve to deliver fluid for flushing. In this example, aspiration could be accomplished by applying suction to the proximal hypotube such that fluid is removed as well as debris while flushing is activated. While these specific embodiments are not sketched, this disclosure describes such configuration. A guidewire 9 extends down the inner lumen of the hypotube to provide a means for navigating the anatomy. Upon placement within the target anatomy, the guidewire is removed and the sheath is pulled back, deploying the cutting and distal protection elements. Deployment of the distal elements is controlled by selective manufacturing processes which preferentially 'train' the elements to behave in a certain fashion such that they exhibit a condition known as 'shape memory." This shape memory is exhibited by the hypotube when it is in an unrestrained position. Abrasives 6 mounted, coated, or integral with the cutting element may be designed to facilitate material removal and shaping of the lesion.

FIG. 11B depicts the delivery sheath pulled back and the cutting and distal protection elements both in a deployed position. Once the procedure is complete, the device is withdrawn back into the delivery sheath and positioned as seen in FIG. 11A. The device can then be safely withdrawn from the anatomy.

FIG. 11C depicts an alternative embodiment of the hypotube design. In this example, all elements are similar as in the previous sketch, with the exception of number 7. Element number 7 details a moveable internal corewire, which is joined with inner distal tip of the hypotube such that longitudinal movement of the corewire may serve to either expand elements 4 and 5, or compress them. When the procedure is complete, removal of this device would be accomplished in a similar fashion as described in FIG. 11B as above.

IC. Interventional Device—Polymer Based Tube

Figure 12A:
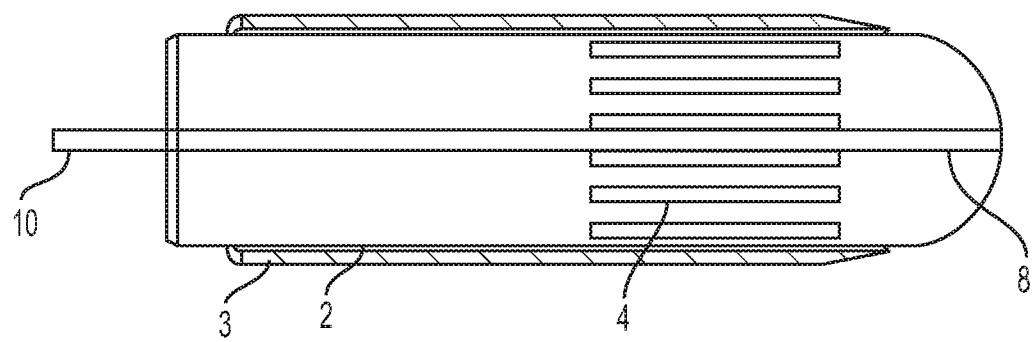
FIGS. 12A and 12B illustrate exemplary before and after side views of an embodiment of the present disclosure.

FIG. 12A depicts the device with the delivery sheath 3 covering the cutting element 4, which is cut from the polymer tube 1 and as such, are integral to the tube. Another example of this design may include a provision for an element that would be positioned in the lumen after removal of the guidewire. This element would serve to deliver fluid for flushing. In this example, aspiration could be accomplished by applying suction to the proximal sheath such that fluid is removed as well as debris while flushing is activated. While this embodiment is not shown in the figures, the present disclosure describes such configuration.

Figure 12B:
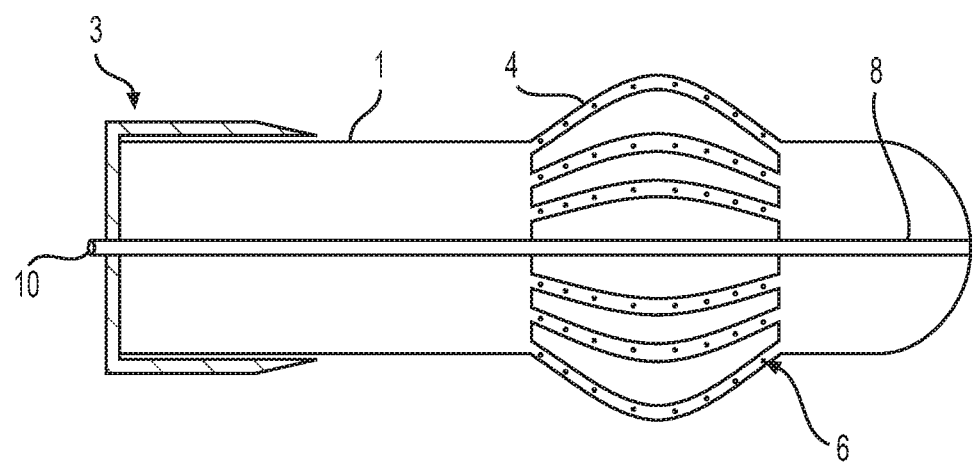

FIG. 12B details a moveable internal corewire 10 which extends down the inner lumen of the tube and is fastened to the distal tip of the device 8 to provide a means for deploying the cutting and distal protection elements through either expansion or contraction. Abrasives 6 mounted, coated or integral with the cutting element may be designed to facilitate material removal and shaping of the lesion.

ID. Interventional Device

Figure 13A:
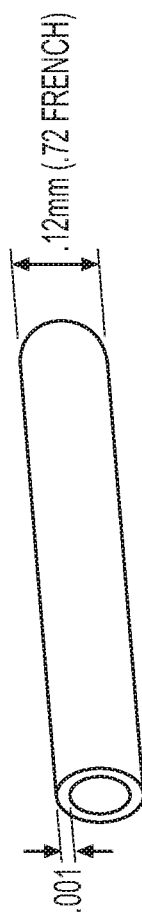
FIGS. 13A-13C illustrate an exemplary hypotube atherectomy corewire and expanded atherectomy balloon with a distal protection element.
Figure 13B:
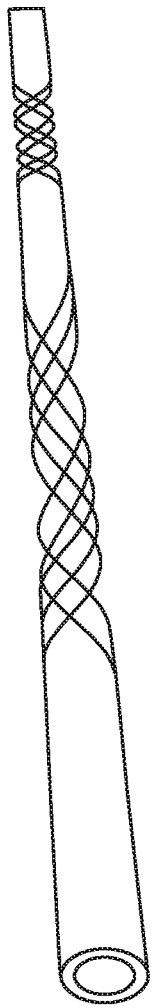
Figure 13C:
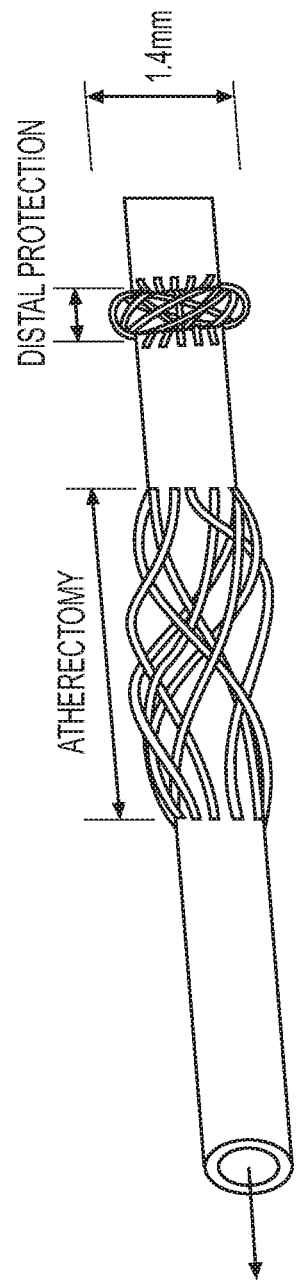

FIGS. 13A-13C show a Single Hypotube based design in which a "puff/pull" aspiration of the atherectomy debris is applied. A single hypotube of 0.12 (0.10-0.14) mm with a 0.001" thickness is laser cut and set to expand an atherectomy device and distal protection device. The device is used by puffing saline or another inert liquid into the space while simultaneous (manually or mechanically) aspirating the disease area and applying rotational force (pushing or turning, mechanically or manually) on the lesion. When fully deployed, the device is 1.4 millimeter in maximum diameter.

E. Interventional Device

Figures 14A, 14B:
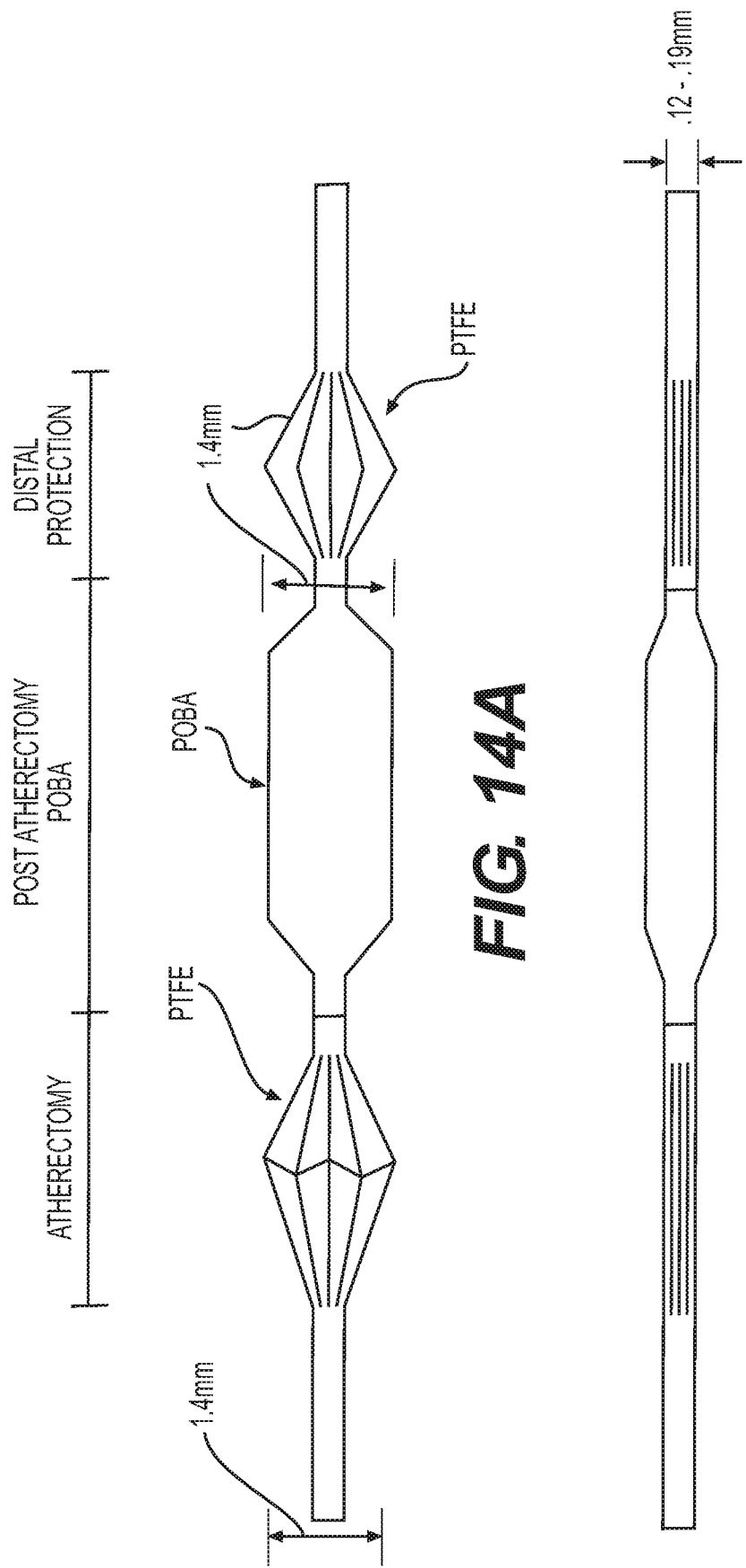
FIGS. 14A and 14B illustrate exemplary side view line drawings of a multicomponent apparatus of the present disclosure.

FIGS. 14A and 14B show a basket like atherectomy device, proximal to a POBA/DE Balloon, proximal to a distal protection device. The basket like atherectomy device and distal protection are deployed distal to the lesion. The device is pulled into the catheter, scrapping debris into the basket. As the balloon passes the lesion site after atherectomy an angioplasty is applied, facilitating a smooth, non-striated blood interface.

IF. Interventional Device—Balloon Based

FIG. 15A depicts the device with the delivery sheath 3 covering the balloon catheter body 1 as well as the cutting 4 and distal protection 5 elements, which are both integral with the balloon body cutting 4. In another example, there may be a provision for an element that would be positioned in the lumen after removal of the guidewire. This element would serve to deliver fluid for flushing. In this example, aspiration could be accomplished by applying suction to the proximal sheath such that fluid is removed as well as debris while flushing is activated. While this embodiment is not shown in the figures, the present disclosure describes such configuration. A guidewire 9 extends down the inner lumen of the device to provide a means for navigating the anatomy, FIG. 15B depicts placement within the target anatomy, where the guidewire is removed and the sheath pulled back, exposing the cutting and distal protection elements. Deployment of the distal elements is controlled by use of an inflation device to fill the balloon with fluid. Once the balloon is inflated, the profile would take shape such that the cutting and distal protection elements are deployed. Abrasives 6 mounted, coated or integral with the cutting element may be designed to facilitate material removal and shaping of the lesion.

Hydrogels or other material may be integral to the distal protection element 5 such that material is attracted and adheres to it.

Figure 16C:
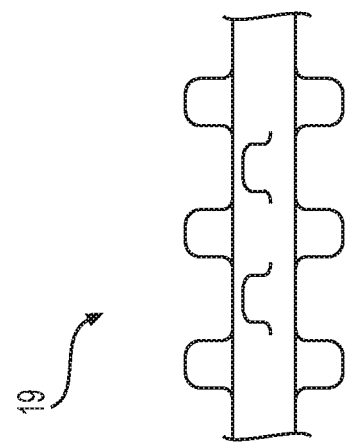
FIGS. 16A-16C illustrate exemplary variations in balloon distal elements, according to an aspect of the present disclosure.
Figure 16B:
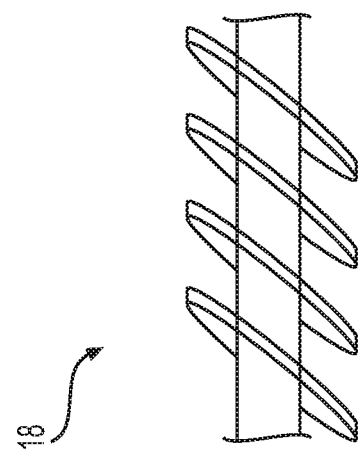
Figure 16A:
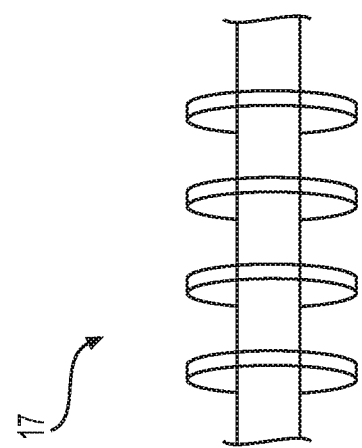

FIGS. 16A-16C depict some general shapes for the balloon distal elements. These sketches serve to provide only general variation ideas and are not meant to be all inclusive.

IG. Interventional Device—OA Access Element

Figure 17B:
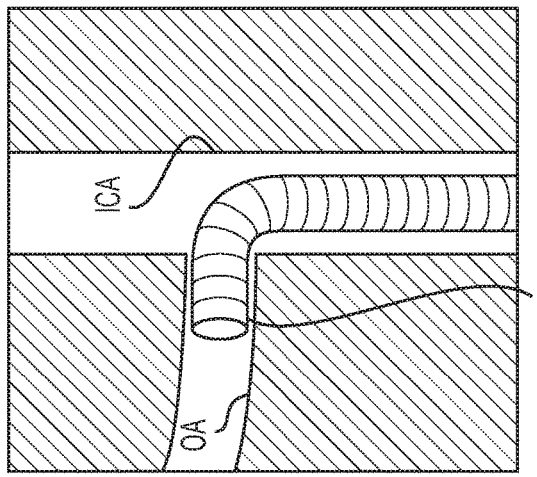
FIGS. 17A-17C illustrate an exemplary series of sequential line drawings showing use of shaped and straight guide wires, according to an aspect of the present disclosure.
Figure 17C:
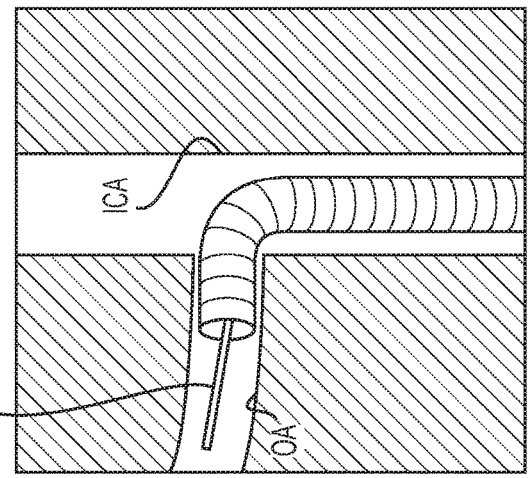
Figure 17A:
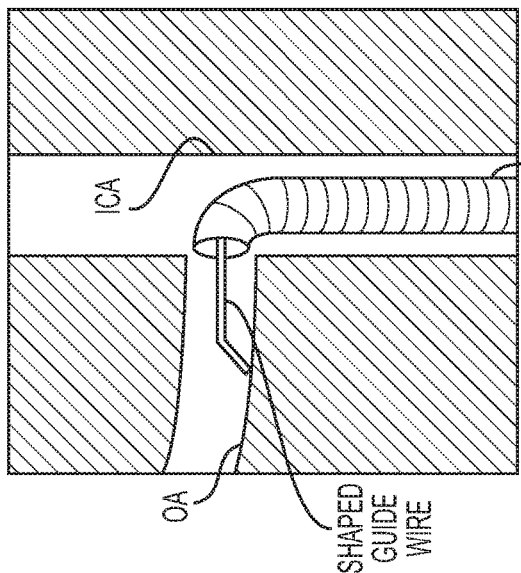

FIGS. 17A-17C show the use of a shaped guidewire to access the OA and follow up with a guiding catheter to position within the entry to the OA. Once inside, the shaped guidewire will be exchanged for either a straight guidewire or an interventional device to continue the procedure. FIGS. 17A-17C depict access of the OA by use of a shaped guidewire, entry into the OA by a guiding catheter over the shaped guidewire and finally exchange of the shaped guidewire for either a straight tip guidewire or an interventional device. The guidewire and guiding catheter is specifically designed for use in the OA and may include a provision for providing downstream protection.

IH. Interventional Device—Flow Directed 1

Figure 18:
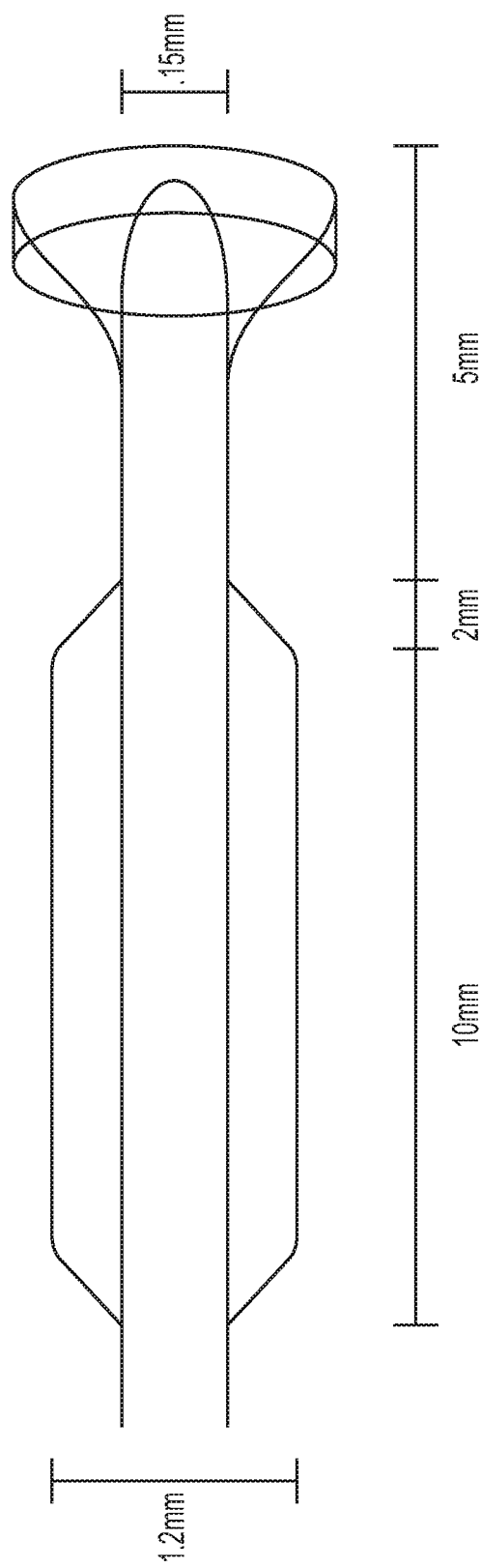
FIG. 18 illustrates an exemplary side view line drawing of an embodiment having an inflatable balloon and a intravascular positioning device/parachute, according to an aspect of the present disclosure.
Figure 19:
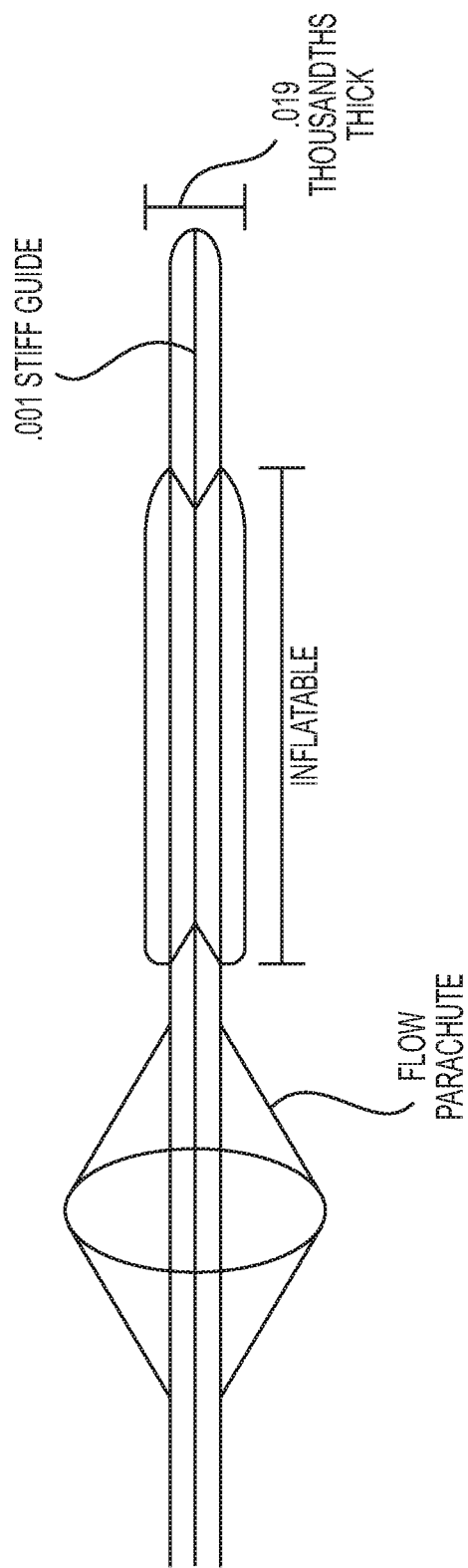
FIG. 19 illustrates an exemplary side view line drawing of an embodiment having an inflatable balloon and a intravascular positioning device/parachute, according to an aspect of the present disclosure.
Figure 20:
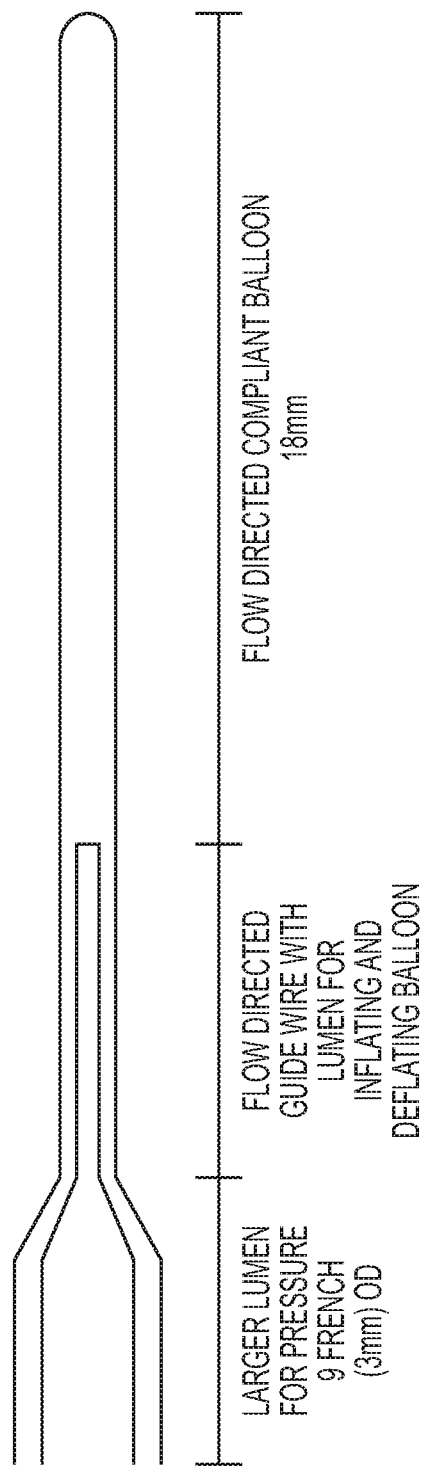
FIG. 20 illustrates an exemplary side view line drawing of an embodiment having an inflatable balloon and a intravascular positioning device/parachute, according to an aspect of the present disclosure.
Figure 21:
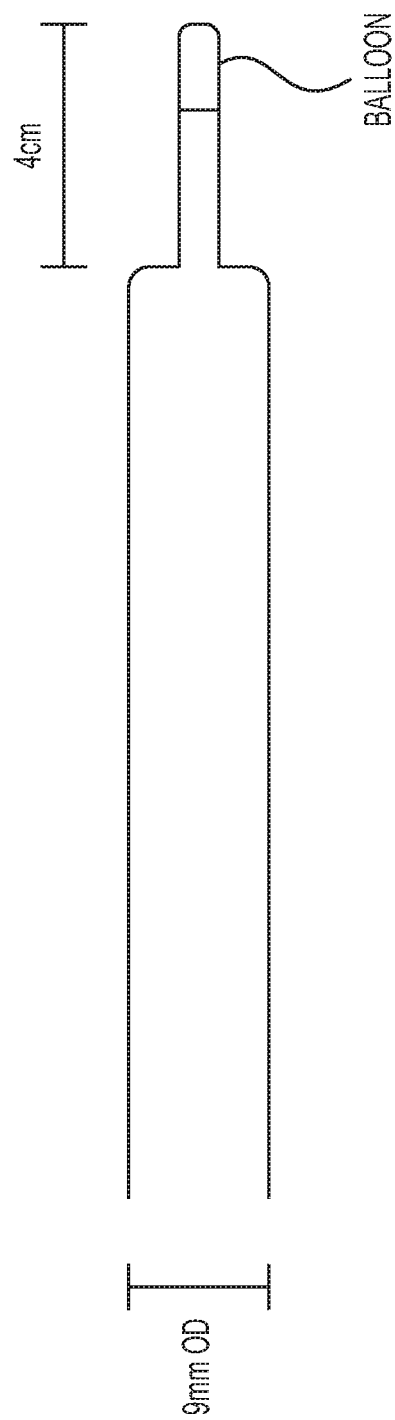
FIG. 21 illustrates an exemplary side view line drawing of an embodiment having an inflatable balloon, according to an aspect of the present disclosure.
Figure 22:
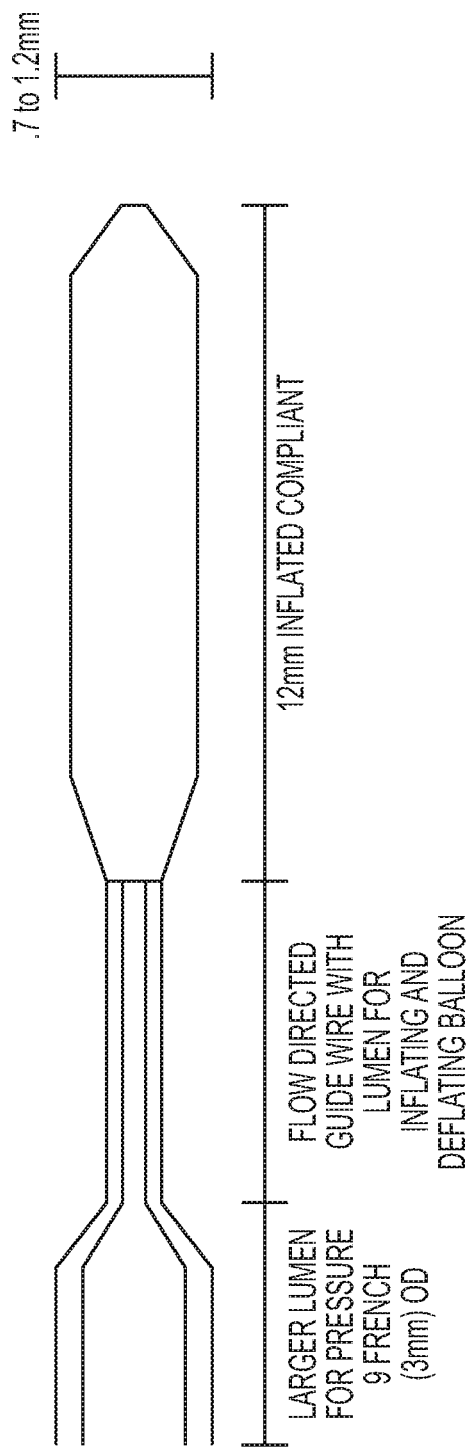
FIG. 22 illustrates an exemplary side view line drawing of an embodiment having an inflatable balloon, according to an aspect of the present disclosure.
Figure 23C:
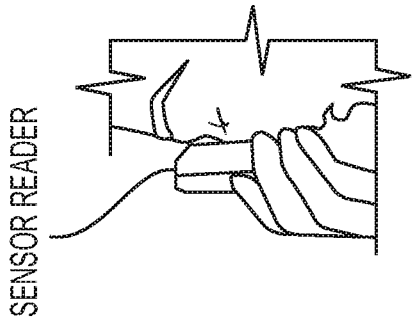
FIGS. 23A-23E illustrate an exemplary series of figures showing anatomy and use of an IOP device, according to an aspect of the present disclosure.
Figure 23E:
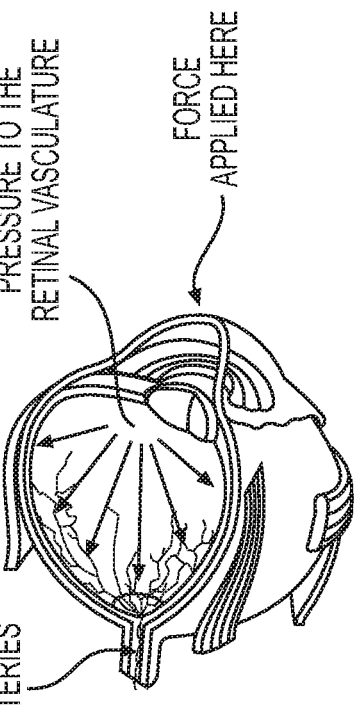
Figure 23B:
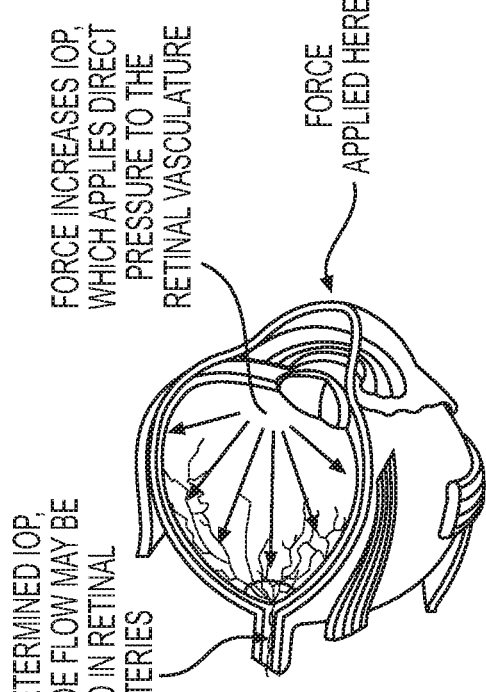
Figure 23D:
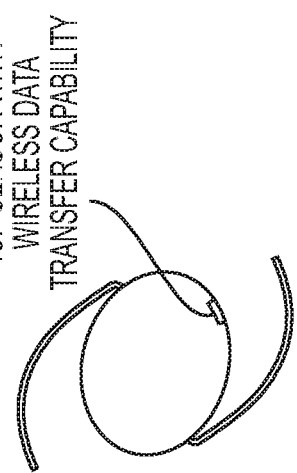
Figure 23A:
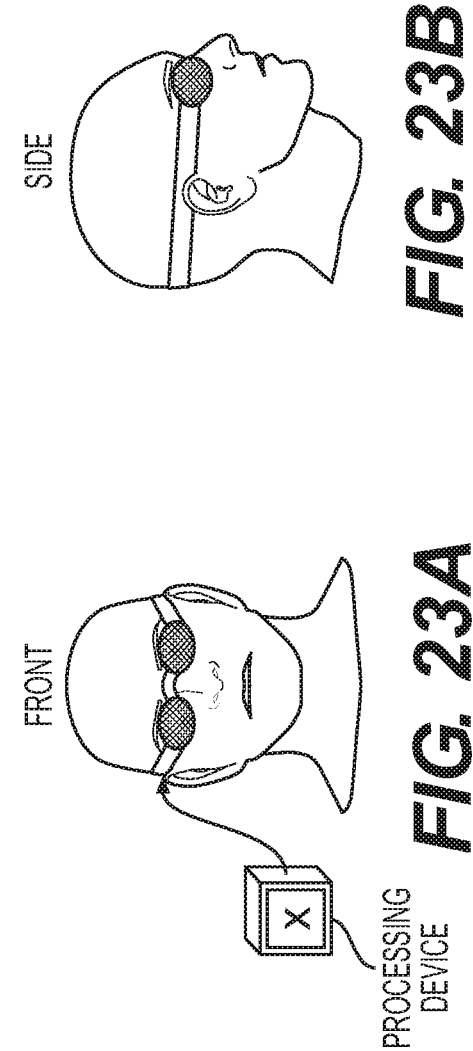

FIG. 18 shows a device that will use the vascular flow to aid in locating and positioning within the OA. There are several features that are detailed here, but all share a common design element in that they are specifically designed for the OA anatomy and will work with the vascular flow to aid in placement and positioning within the anatomy. An additional design provision may include the ability to work with the IOP device (as detailed in section I). In this use, the flow directed element would take into account the reversal of vascular flow and would follow that flow accordingly, which would aid in the removal of the device from the target anatomy. This feature would simplify the removal of the instrument by reducing the amount of force required to withdraw the device. There are several examples of this design as noted by FIG. 18.

II. Interventional Device—Flow Directed 2

FIGS. 19-22 describe a simple, flow directed balloon that is unified with a large volume delivery catheter. It is a hybrid guidewire/balloon/aspiration device. Novelty is found in the fact that the flow directed balloon and guidewire are a single unit and that the inner diameter of the lumen starts out at around 7 to 8 French and narrows dramatically for the last 3 cm to 4 cm.

Delivery of the device into the ostium of the OA may be done by a catheter, that has a 90 degree port at the ostium of the OA. This allows for the very small diameter (0.19 mm OD or smaller) balloon guidewire to enter into the OA and to be pulled into the artery and across the lesion by normal blood flow. The larger diameter of the inner diameter catheter allows for good pressure to be maintained proximal to the balloon facilitating the delivery of contrast agents in addition to saline for balloon inflation.

IJ. IOP Device—General Description

FIGS. 23A-23E depict the an embodiment of the device used to manipulate IOP. One element will fit the patients eye(s) such that it may be used to apply pressure to the front of the eye. The eye portion may be held in position with a strap, adhesive, external member or other method that sufficiently accomplishes the task of keeping the eye portion in proper contact with the patient's eye(s). The eye contact portion of the device may be designed to cover and manipulate a single eye, both eyes, one at a time, two at the same time or any combination. Pressure manipulation of the front of the eye will be accomplished by applying a specified amount of direct pressure to the front (typically corneal) area of the eye. This may be accomplished in a variety of ways, including use of pneumatic, hydraulic, gravity and/or other mechanical means of manipulating force over an area. There may be need to combine these forces in such a way as to optimize the pressure manipulation. Use of mechanical force manipulation will provide the best methodology and control for removal of force such that the IOP returns to the normal steady state post procedure in a repeatable, desirable manner. A second element will provide for the IOP measurement of the eye under manipulation. There may be several ways to accomplish IOP measurement. These include remote implantable sensor with wired or wireless data transmission capability, corneal tonometry, non-corneal tonometry and/or transpalpebral tonometry. In addition, there may be other ways to accomplish IOP measurements such that pressure values are obtained from the subject eye. A third element will provide the user (physician) with the ability to select pressure and time for the device to interact with the eye in the form of an external control feature. This external control feature may be in the form of a computer, tablet, smart phone or other device that provides the user with the necessary control and feedback information needed to perform the IOP manipulation. This control feature will also contain a feedback loop which will continuously monitor IOP so that a constant pressure may be maintained. This control mechanism will also allow for ramp up/ramp down of pressure, non-constant pressure, time manipulation and/or any combination thereof. This capability will likely be software driven and will provide the user with the ability to custom tailor an IOP manipulation profile for a specific patient. Without intending to be bound by theory, the rate or pressure induced, time at pressure, and rate of pressure reduction will be important to the success of the procedure and will design the control mechanism to provide this capability. In addition, the ability to capture, chart and store patient centric data will be an element of this control mechanism.

Use of the device elements as detailed above will allow for the physician to induce retrograde vascular flow for up to 3 minutes at a time, such that when the interventional device is used, the risk for retinal vasculature embolism is reduced. It is known that at a minimum, retrograde flow in the central retinal artery can be maintained for antithrombotic protection and possibly the ciliary arteries. With pressure put on the front of the eye, the blood volume of the choroid layers can be forced back, through the central retinal artery, ciliary arteries and possibly lacrimal arteries.

Figure 24A:
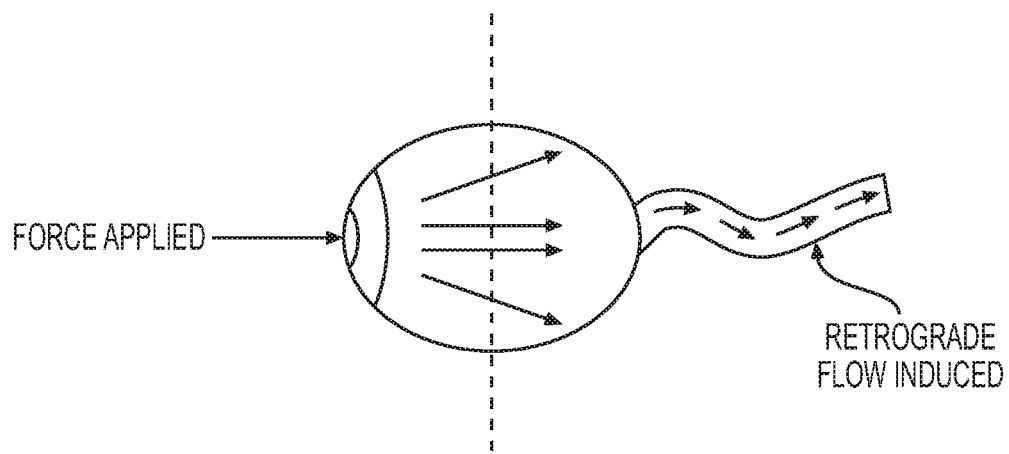
FIGS. 24A and 24B illustrate exemplary side view line drawings of the eye showing IOP caused by mechanical force, according to an aspect of the present disclosure.
Figure 24B:
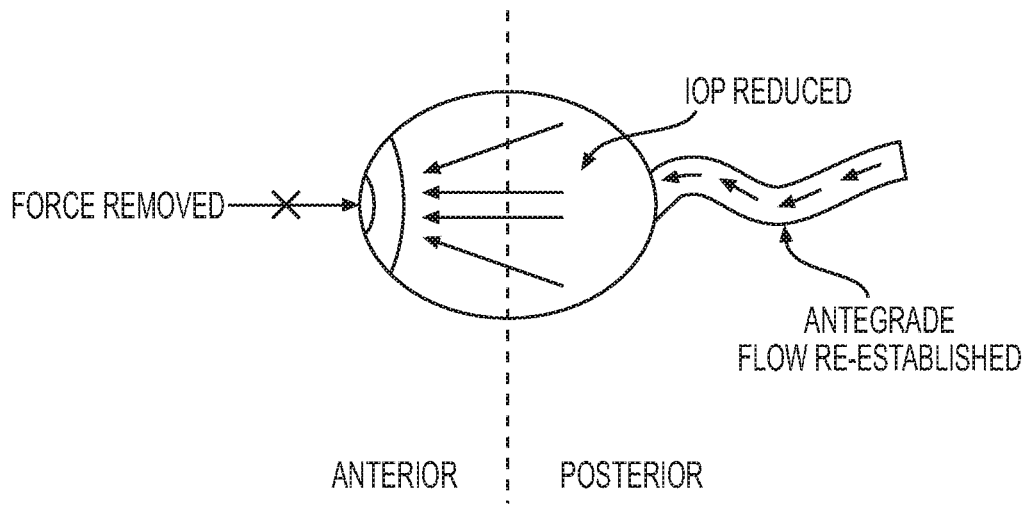

FIGS. 24A and 24B detail how the force applied to the front of the eye will translate into force flowing through the eye, increasing IOP, resulting in retrograde vascular flow. The drawing also details how the removal of force will result in a return to the normal pressure state of the eye. Note the drawing is not anatomically correct.

Figure 25:
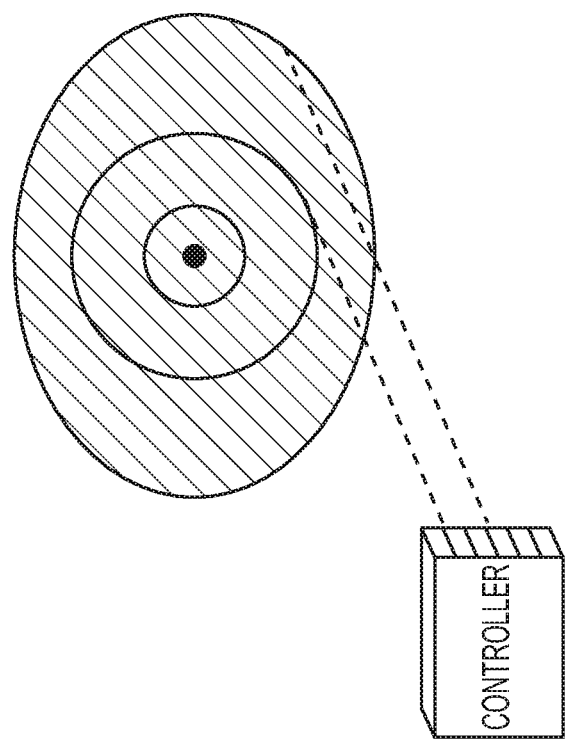
FIG. 25 illustrates an exemplary front view line drawing of the eye showing IOP caused by mechanical force, with a controller unit for interacting in a continuous or periodic manner, according to an aspect of the present disclosure.

FIG. 25 depicts one embodiment of a feedback loop utilizing an implantable IOP sensor.

Figure 26:
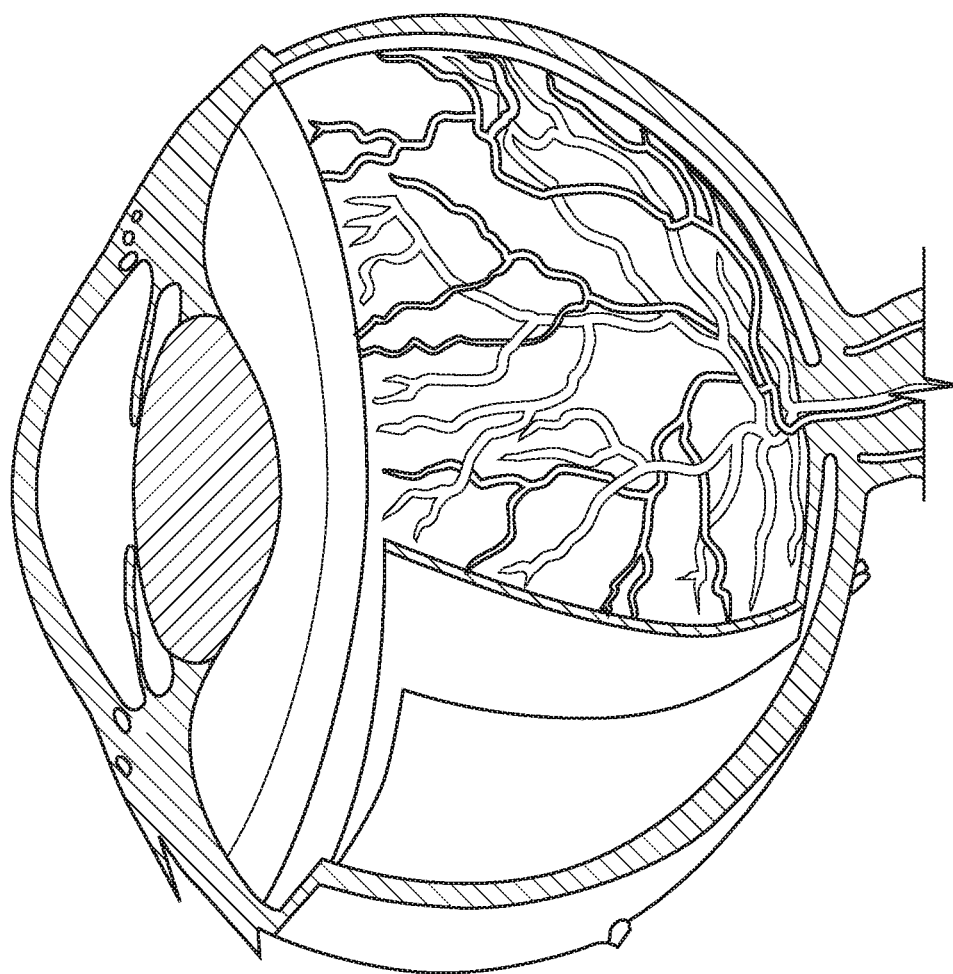
FIG. 26 is an exemplary anatomical drawing of the eye for reference purposes only.

FIG. 26 provides detail associated with the posterior vasculature of the eye for informational purposes only.

While this specification contains many specifics, these should not be construed as limitations on the scope of an embodiment that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents that all fall in the scope of the aspects described herein. Accordingly, the present disclosure is not to be considered as limited by the foregoing description.

EXAMPLES

Example 1

Without being bound by theory, it is believed that compromised blood flow to the vasculature of the posterior eye directly contributes to diseases of the eye. Further, it is believed that this lack of normal blood flow may originate in the ICA, the OA, branches of the OA, have a cardiac origin, and/or combinations thereof, and be directly caused by a blockage in one or more of these vessels. This lack of sufficient blood flow directly contributes to inadequate nutrient levels seen in tissues such as the choroid, retina, optic nerve, and other ophthalmic anatomy. This blockage may manifest as stenosis, lesions, or other physiology within the ophthalmic related vasculature and compromise normal blood flow such that the posterior eye vasculature does not receive an adequate nutrient supply for maintenance of normal function. As a result, it is possible for a cascade of events to initiate which may result in various diseases of the eye.

Linear and volumetric blood flow was measured for healthy controls and diseased patients, wherein the diseased patients had confirmed AMD diagnoses. Flow rates were measured for the Left Ophthalmic Artery (LOA), Right Ophthalmic Artery (ROA), Left Internal Carotid Artery (LICA) and Right Internal Carotid Artery (RICA) using Phased Contrast Magnetic Resonance Imaging (PCMRI) technique on a 7 Tesla Nmri machine. These flow rates were measured in centimeters per second (cm/sec) for linear flow and in millimeters/minute (ml/min) for volumetric flow. The average diameter of the ICA for a healthy control is 4.6 mm and the average diameter of the OA for a healthy control is 1.2 mm. Average values for the same vessels in diseased patients were 4.18 mm for the ICA and 0.86 mm for the OA.

Specific linear and volumetric flow rates were compared, and the OA flow data showed a medically or clinically observable difference between the flow rates for healthy controls compared to diseased patients. Specific flow rates were compared, and the ICA flow data shows a medically or clinically observable difference between the flow rates for healthy controls compared to diseased patients. In every case, the blood flow rate for the diseased patients appeared to be lower than the blood flow rate for the healthy controls.

Example 2

In a cadaveric tissue, the RICA was removed and the ostium was visually examined. Blockage of the OA at the ostium was confirmed, wherein the blockage appeared to be complete. Once the section of LICA was removed, internal access to the OA ostium was gained, and a micro PTCA balloon catheter was inserted.

This test was performed to visually observe the effect of placing and inflating a balloon catheter in the OA. This (non-compliant) balloon catheter had a maximum diameter of 0.85 mm at 16 atms, with a crossing profile of 0.74 mm and a working length of approximately 5 mm. The balloon was inflated several times to approximately 12 atms maximum and the balloon was observed through the vessel. After observations, the vessel appeared to tolerate the inflations without obvious signs of damage.

Example 3

A system of the present disclosure is designed to induce reverse blood flow in the cerebral vasculature during neuro interventional procedures. This system provides protection from particulate related stroke during these procedures. Enhancements to the basic system include:

CCA to IJV circuit. This pathway reduces the overall device length required to reach the target anatomy. While this procedure requires cervical access, there is no need to do femoral access and expose the patient to the potential issues related to crossing the arch. This type of connection between an artery and vein is commonly referred to as a fistula.

Addition of an in line filter to capture particulate.

Sizing the tubing, stock cocks and filter such that a minimal resistance to flow is encountered by blood as it travels through the device. It is anticipated the device will be 8.5 to 9.0 French. Maximizing the internal diameter of the various components allows for blood to flow at the most rapid velocity.

Addition of a circuit to connect the CCA flow to the SOA. This connection will provide flow directly to the OA so that flow is reversed. This OA reverse flow will prevent embolization of the OA/central retinal artery during interventional procedures.

Specially designed CCA occlusion balloon designed to reduce probability of low or no flow zones in the CCA.

Example 4

In some embodiments of the present disclosure, the flow direction element of the system is used to initiate the reversal of flow in the CCA. Typically, CCA flow reversal may be accomplished by use of an inflatable balloon device. CCA flow reversal may also be accomplished without the need for a balloon by using a sheath that has external force applied to compress the CCA against the tube portion of the sheath. This compressive action serves to prevent blood flow around the sheath, in the same way as an inflatable balloon does from inside the CCA and force blood through the sheath and into the venous circuit of the system, thereby providing flow reversal. The sheath may be of conventional design, or may contain elements that facilitate compressing the CCA against the sheath for the purpose of establishing flow reversal.

Methodology and Purpose of Examples 5 and 6

1) Dissection of specimens diagnosed with AMD for the purpose of identifying CAD disease (plaque) in the carotid siphon/ophthalmic ostium and to provide evidence of the ability to cannulate and deliver an angioplasty balloon to the OA ostium.

2) Dissection of a specimen (with cervical segment) diagnosed with AMD to identify CAD disease (plaque) in the carotid siphon/ophthalmic ostium.

A true endovascular approach requires an imaging modality that relies on injection of contrast, which is not possible in static tissue samples such as a cadaver. Based on these limitations, the following two Examples show balloon placement and inflation directly in the exposed ophthalmic ostium in situ and post dissection.

Example 5

The primary goal for dissection of a specimen with bilateral AMD was to prove that it is possible to place and dilate an angioplasty balloon catheter in the segment of the OA just distal to the ICA ostium, prior to the typical OA 90° bend, without dissecting the OA.

An angioplasty balloon with a maximum inflated diameter of 0.8 mm at 16 ATMs, and a working length of approximately 3.5 mms was used.

The left and right ICA/OA ostiums in the first specimen were identified and material from the sphenoid was removed to expose the OA. The balloon catheter was positioned into the LOA and the balloon was inserted such that the working length of the balloon did not extend beyond the desired segment of the LOA.

The balloon was able to be delivered and inflated at the desired location of the LOA, within the ostium of the LOA.

Both ostiums were then examined for evidence of plaque in the ICA, OA, and ostium in situ. Plaque formation was identified at the ostium of the transected LICA, and in the walls of the LICA. Plaque formation was also identified in the RICA, at the ostium of the transected ROA, and in the walls of the RICA.

Example 6

The primary goal for dissection of this specimen was to prove that it is possible to place and dilate an angioplasty balloon catheter in the segment of the OA just distal to the ICA ostium, prior to the typical OA 90° bend, without dissecting the OA. The secondary goal was to examine each ICA/OA ostium for evidence of plaque. We identified the left and right ICA/OA ostiums without having to remove material from the sphenoid and could visualize plaque in both ICA segments in situ. In addition, plaque formation in the LOA could easily be seen.

The left and right ICA vessel segments were removed and transected. In both samples, blockage was observed directly at the ophthalmic ostium.

After examining the inside and outside of the LICA vessel, plaque formation could clearly be seen at the base of the OA near the ostium. The LOA was dissected from the LICA at the ostium to expose the plaque. Plaque formation was also clearly seen in the ostium of the LOA.

A balloon catheter was placed in the RICA vessel segment. The balloon catheter was positioned into the ROA and inserted such that the working length of the balloon did not extend beyond the desired segment of the ROA (as noted in the previous Example).

The angioplasty balloon was successfully positioned and inflated within the target ROA anatomy. Plaque was identified in both the LICA and RICA as well as both the ROA and LOA ostium. This plaque appeared to be blocking or nearly blocking the OA in both the left and right ostiums.

We claim:

1. A method for treating glaucoma or age-related macular degeneration (AMD), comprising:
   accessing an ophthalmic artery (OA) through an access vasculature site of a subject via a first device;
   positioning the first device or a second device within the OA; and
   removing material from the OA, to thereby treat glaucoma or AMD, wherein the material includes one or more of a blockage, a stenosis, a lesion, plaque, or other physiology in the OA, wherein removing the material from the OA includes inducing a vibration in a guidewire via an electric motor to loosen and/or dislodge the material.

2. The method of claim 1, wherein removing the material from the OA further includes at least partially removing material from a junction between the OA and an internal carotid artery of the subject.

3. The method of claim 1, wherein removing the material from the OA includes using an atherectomy device to physically remove at least a portion of the material.

4. The method of claim 3, further including deploying a distal protection element downstream of the atherectomy device.

5. The method of claim 1, wherein removing the material from the OA, includes opening a channel through the material to restore patency of the OA.

6. The method of claim 1, wherein inducing vibration in the guidewire to loosen and/or dislodge the material includes inducing vibration in the guidewire and directly contacting the material with the guidewire, and/or application of a specific resonant frequency of vibration of the material to the guidewire.

7. The method of claim 1, wherein removing the material from the OA includes expanding a balloon, inducing a vibration in the balloon via an electric motor to loosen or dislodge the material, and directly contacting the balloon with the material and/or application of a specific resonant frequency of vibration of the material to the balloon.

8. A method for treating glaucoma or age-related macular degeneration (AMD), comprising:
   accessing an ophthalmic artery (OA) through an access vasculature site of a subject via a first device;
   positioning the first device or a second device within the OA of the subject, wherein the positioned first device or second device includes an atherectomy device and at least one embolic protection element;
   removing material from the OA via the atherectomy device, to thereby treat glaucoma or AMD, wherein the material includes at least one of a blockage, a stenosis, a lesion, plaque, or other physiology in the OA; and
   during the removing, inhibiting passage of the removed material via the at least one embolic protection element.

9. The method of claim 8, further comprising deploying the atherectomy device and the at least one embolic protection element distal of the material to be removed from the OA.

10. The method of claim 9, wherein the at least one embolic protection element includes a distal protection element positioned distally of the atherectomy device.

11. The method of claim 8, wherein the at least one embolic protection element includes a hydrogel configured to attract and adhere to the material removed from the OA.

12. The method of claim 8, wherein the atherectomy device includes a basket, and wherein removing the material from the OA via the atherectomy device includes scraping the material into the basket.

13. The method of claim 8, wherein the atherectomy device and the at least one embolic protection element are integral with the positioned first device or second device.

14. The method of claim 8, wherein the positioned first device or second device includes a delivery sheath, and the atherectomy device and the at least one embolic protection element are mounted on the delivery sheath.

15. The method of claim 14, wherein the positioned first device or second device includes a fluid delivery element for delivering fluid to the OA.

16. The method of claim 15, wherein removing the material from the OA via the atherectomy device includes applying suction to the delivery sheath (1) to remove fluid delivered by the fluid delivery element and/or (2) to remove the material from the OA.

17. A method for treating glaucoma or age-related macular degeneration (AMD), comprising:
   accessing an ophthalmic artery (OA) through an access vasculature site of a subject via a first device;
   positioning a first embolic protection element within an internal carotid artery (ICA) of the subject via the first device;
   positioning a second device within the OA of the subject, the second device including an atherectomy device and a second embolic protection element located distal of the atherectomy device;
   deploying the atherectomy device and the second embolic protection element in the OA;
   removing material from the OA via the atherectomy device, to thereby treat glaucoma or AMD; and
   during the removing, inhibiting passage of the removed material downstream into the ICA and the OA via the first embolic protection element and the second embolic protection element, respectively.

18. The method of claim 17, wherein the atherectomy device includes a basket, and wherein removing the material from the OA via the atherectomy device includes scraping the material into the basket.

19. The method of claim 17, wherein deploying the atherectomy device and the second embolic protection element in the OA includes expanding the atherectomy device and the second embolic protection element in the OA by retracting a sheath of the second device.

* * * * *

UNITED STATES PATENT AND TRADEMARK OFFICE
CERTIFICATE OF CORRECTION

PATENT NO. : 11,654,047 B2  
APPLICATION NO. : 16/932401  
DATED : May 23, 2023  
INVENTOR(S) : Michael Calhoun, Jeff Franco and Robert M. Vidlund Page 1 of 1

It is certified that error appears in the above-identified patent and that said Letters Patent is hereby corrected as shown below:

On the Title Page

On page 2, Column 1, Line 17, "PCT/US2017/051551" should read "PCT/US2017/021673".

Signed and Sealed this
Twenty-fifth Day of July, 2023

Katherine Kelly Vidal
*Director of the United States Patent and Trademark Office*